US008318696B2

(12) United States Patent
Duchaussoy et al.

(10) Patent No.: US 8,318,696 B2
(45) Date of Patent: *Nov. 27, 2012

(54) POLYSACCHARIDES WITH ANTITHROMBOTIC ACTIVITY COMPRISING AT LEAST ONE COVALENT BOND WITH BIOTIN OR A BIOTIN DERIVATIVE

(75) Inventors: Philippe Duchaussoy, Toulouse (FR); Jean-Marc Herbert, Tournefeuille (FR); Maurice Petitou, Paris Cedex (FR); Pierre Savi, Seysses (FR)

(73) Assignee: Sanofi, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/036,143

(22) Filed: Feb. 28, 2011

(65) Prior Publication Data
US 2011/0144042 A1    Jun. 16, 2011

Related U.S. Application Data

(63) Continuation of application No. 11/035,717, filed on Jan. 14, 2005, now Pat. No. 7,943,595, which is a continuation of application No. 10/381,154, filed as application No. PCT/FR01/02918 on Sep. 20, 2001, now Pat. No. 6,844,329.

(30) Foreign Application Priority Data

Sep. 22, 2000  (FR) ..................... 00 12094

(51) Int. Cl.
*A61K 31/715*  (2006.01)
*C07H 1/00*  (2006.01)
(52) U.S. Cl. ........................... 514/54; 536/124; 536/123
(58) Field of Classification Search .................. 536/124, 536/123; 514/54
See application file for complete search history.

(56) References Cited

U.S. PATENT DOCUMENTS

| 3,960,884 | A | 6/1976 | Zavyalov et al. |
| 6,844,329 | B2 | 1/2005 | Duchaussoy et al. |
| 7,943,595 | B2 * | 5/2011 | Duchaussoy et al. ........... 514/54 |
| 2001/0023288 | A1 | 9/2001 | Wilbur et al. |

FOREIGN PATENT DOCUMENTS

| EP | 1 022 289 | 7/2000 |
| JP | 11-311624 | 11/1999 |
| WO | WO 99/36443 | 7/1999 |
| WO | WO 00/02051 | 1/2000 |

OTHER PUBLICATIONS

Petitou et al reference ("The Synthetic Pentasaccharide Fondaparinux: First in the Class of Antithrombotic Agents that Selectively Inhibit Coagulation Factor Xa", Seminars in Thrombosis and Hemostasis/vol. 28, No. 4, 2002, pp. 393-402).*
Derwent Abstract No. 199939.
LeBaron et al., Journal of Biological Chemistry, May 15, 1989, 264, 14, pp. 7950-7956.
Official Action dated Sep. 10, 2010 received in U.S. Appl. No. 11/035,717.
Official Action dated Apr. 15, 2010 received in U.S. Appl. No. 11/035,717.
Final Official Action dated Aug. 28, 2009 received in U.S. Appl. No. 11/035,717.
Official Action dated Jul. 10, 2008 received in U.S. Appl. No. 11/035,717.
Official Action dated Sep. 21, 2007 received in U.S. Appl. No. 11/035,717.
Van Boeckel C.A.A. et al., "The Unique Antithrombin III Binding Domain of Heparin: A Lead to New Synthetic Antithrombotics", *Angewandte Chemie Int. Ed. Engl.* 32(12:1671-1690 (Dec. 1993).
Petitou M. et al., "Synthetic Anticoagulants-Anticoagulant Drugs are Essential for Fighting Venous Thrombo-Embolism. An Analysis of Natural Anticoagulants has Led to the Synthesis of New Drugs", *Pour La Science* 274:28-34 (2000).

* cited by examiner

*Primary Examiner* — Shaojia Anna Jiang
*Assistant Examiner* — Everett White
(74) *Attorney, Agent, or Firm* — Scully, Scott, Murphy & Presser, P.C.

(57) ABSTRACT

The present invention relates to novel synthetic polysaccharides with antithrombotic activity exhibiting at least one covalent bond with biotin or a biotin derivative and to a process employing avidin or streptavidin which makes it possible to neutralize these polysaccharides.

16 Claims, No Drawings

POLYSACCHARIDES WITH ANTITHROMBOTIC ACTIVITY COMPRISING AT LEAST ONE COVALENT BOND WITH BIOTIN OR A BIOTIN DERIVATIVE

CROSS-REFERENCE TO RELATED APPLICATIONS

This application is a continuation of copending application Ser. No. 11/035,717 filed Jan. 14, 2005, which is a continuation of copending application Ser. No. 10/381,154 filed Mar. 21, 2003, which is a national stage application under 35 U.S.C. §371 of International Application Serial No. PCT/FR01/02918 filed Sep. 20, 2001, which claims benefit of French Patent Application No. 00/12094 filed Sep. 22, 2000, the entire contents of which are incorporated herein by reference.

FIELD OF THE INVENTION

The present invention relates to novel synthetic oligo- and polysaccharides exhibiting at least one covalent bond with biotin or a biotin derivative and having the anticoagulant and antithrombotic pharmacological activities of heparin

BACKGROUND OF THE INVENTION

Heparin catalyses, in particular via antithrombin III (AT III), the inhibition of two enzymes which are involved in the blood coagulation cascade, namely factor Xa and factor IIa (or thrombin). Preparations comprising low molecular weight heparins (LMWHs) comprise chains formed of 4 to 30 monosaccharides and have the property of acting more selectively with respect to factor Xa than with respect to thrombin.

It is known that the inhibition of factor Xa requires attachment of heparin to AT III via the antithrombin-binding domain (Domain-A) and that inhibition of factor IIa (thrombin) requires attachment to AT III, via the Domain-A, and to thrombin via a less well defined binding domain (Domain-T).

Synthetic oligosaccharides corresponding to the Domain-A domain of heparin are known. They are disclosed, for example, in Patents EP 84 999 and EP 529 715, the patent application published under the number WO 99/36428 and the publication *Bioorg. Med. Chem.*, 1998, 6, 1509-1516. These synthetic oligosaccharides have the property of selectively inhibiting, via antithrombin III, factor Xa of the coagulation without any activity with respect to thrombin. They display an antithrombotic activity in venous thrombosis.

Synthetic oligosaccharides capable of inhibiting thrombin and factor Xa via activation of AT III have been disclosed in the patent applications published under the numbers WO 98/03554 and WO 99/36443.

Novel biologically active sulphated and alkylated polysaccharide derivatives are disclosed in these patent applications. They are in particular anticoagulants and antithrombotics. It has in particular been shown that these sulphated and alkylated polysaccharides can be powerful antithrombotics and anticoagulants depending upon the arrangement of the alkyl groups and sulphate groups carried by the glucide backbone. More generally, it has been found that, by preparing polysaccharide sequences, it is possible to precisely adjust the activities of GAGs type in order to obtain very active products exhibiting the anticoagulant and antithrombotic pharmacological properties of heparin. In comparison with heparin, they exhibit the advantage of having a specific structure and of not reacting with platelet factor 4, the cause of the thrombocytopenic effects of heparin.

However, the use in human therapeutics of some products disclosed in the patent applications published under the numbers WO 98/03554 and WO 99/36443 and in Patent EP 529 715 can prove to be problematic, in particular if these products have a long half-life. In the field of the prevention or treatment of thrombosis with the above products, the fluidity of the blood has to be reestablished or maintained while preventing a haemorrhage from being brought about.

This is because it is well known that a haemorrhage can be triggered in a patient under treatment by any accidental cause. It may also be necessary to intervene surgically in a patient under antithrombotic treatment. Furthermore, during some surgical procedures, anticoagulants may be used at a high dose so as to prevent blood coagulation and it is necessary to neutralize them at the end of the operation. It is therefore advantageous to have antithrombotic agents which can be neutralized in order to stop the anticoagulant activity at any time. In point of fact, the known synthetic oligosaccharides described above cannot be easily neutralized by the known antidotes for heparin or LMWHs, including protamine sulphate.

SUMMARY OF THE INVENTION

The present invention relates to novel synthetic polysaccharides with a structure similar to that of the compounds disclosed in the patent applications published under the numbers WO 98/03554 and WO 99/36443 and in Patent EP 529 715: the structures of the synthetic oligosaccharides which are a subject-matter of the invention are modified in the sense that they exhibit a covalent bond with biotin (hexahydro-2-oxo-1H-thieno[3,4-d]imidazole-4-pentanoic acid) or with a biotin derivative. Surprisingly, it appears that the introduction of biotin or a biotin derivative does not modify the pharmacological activity of the polysaccharides. In fact, the novel polysaccharides which are a subject-matter of the invention have an antithrombotic activity comparable with that of the oligosaccharides of the prior art. However, they additionally have the advantage of being able to be rapidly neutralized by a specific antidote in an emergency situation. This specific antidote is avidin (The Merck Index, Twelfth edition, 1996, M.N. 920, pages 151-152) or streptavidin, two tetrameric proteins with respective masses equal to approximately 66 000 and 60 000 Da which have a very high affinity for biotin.

DETAILED DESCRIPTION OF THE INVENTION

Generally, the invention relates to synthetic polysaccharides with antithrombotic activity having at least one covalent bond with biotin or a biotin derivative.

Mention may be made, as biotin derivative, of the biotin derivatives shown in the Pierce catalogue, 1999-2000, pages 62 to 81, for example 6-biotinamidohexanoate,

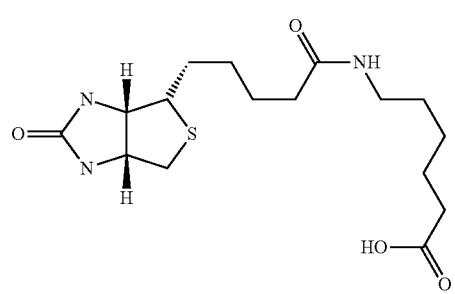

or 6-[6-biotinamidohexaamido]hexanoate,
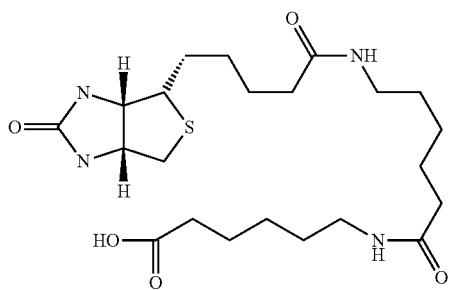
or 2-biotinamidoethanethiol
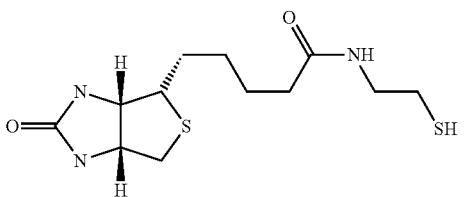
or the compounds of the following formulae:
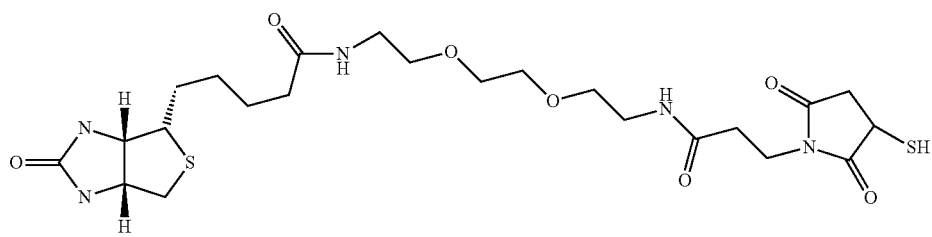
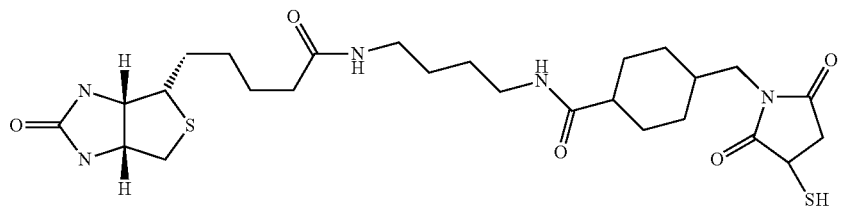
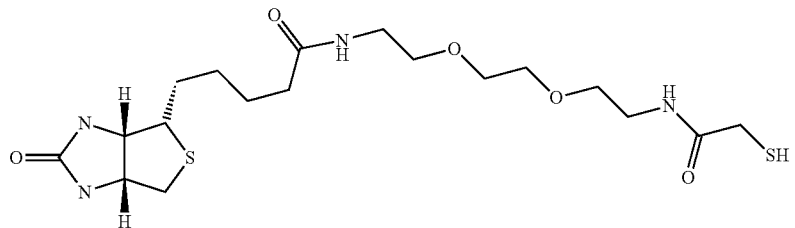
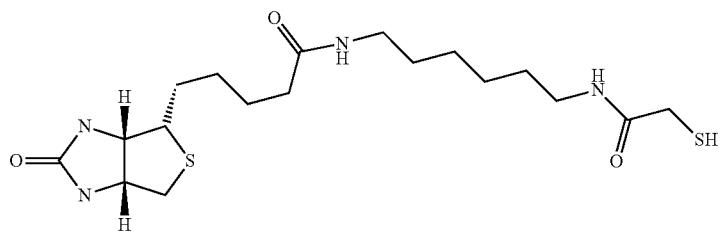
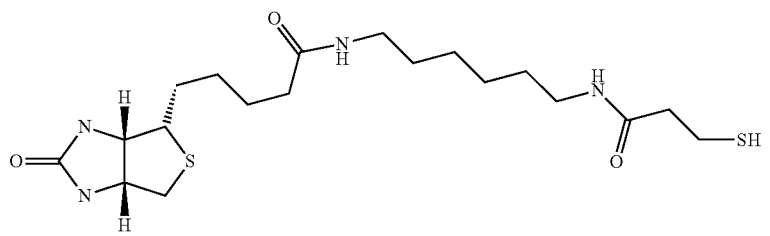

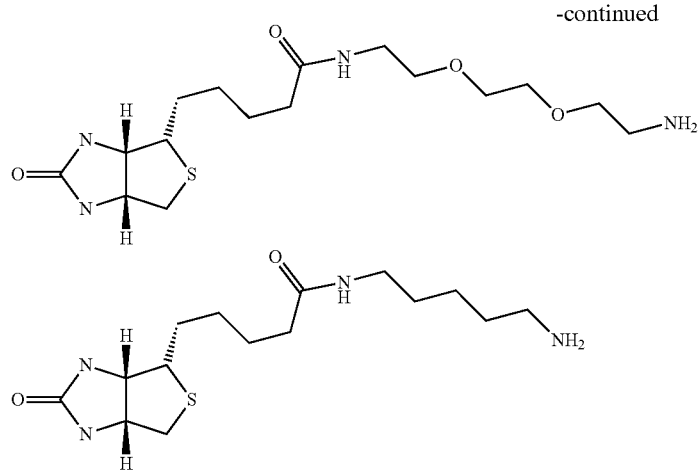

In particular, a subject-matter of the present invention is the polysaccharides of formula (I):

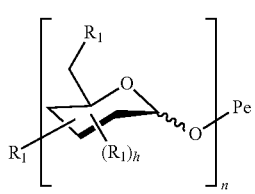

(I)

in which:

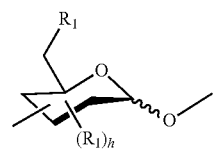

is a diagrammatic representation of a monosaccharide unit with a pyranose structure chosen from hexoses, pentoses and the corresponding deoxy sugars, this unit being bonded via its anomeric carbon to another monosaccharide unit and the hydroxyl groups of this unit being substituted by identical or different $R_1$ groups, $R_1$ being as defined below, Pe represents a pentasaccharide of structure:

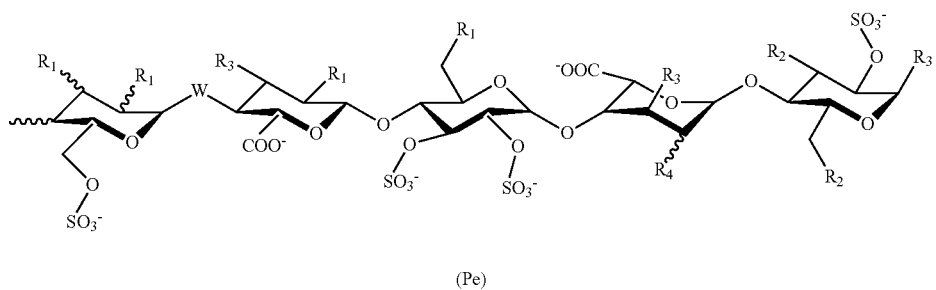

(Pe)

the wavy line denotes a bond situated either below or above the plane of the pyranose ring,

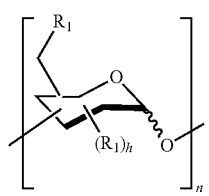

(Po)

Po denotes a polysaccharide, comprising n identical or different monosaccharide units, bonded via its anomeric carbon to Pe, h is equal to 1 or 2, n is an integer and can take any value from 0 to 25, $R_1$ represents the -T-Biot linkage, a $(C_1-C_6)$alkoxy group or an $—OSO_3^-$ group, $R_2$ represents the -T-Biot linkage, a $(C_1-C_6)$alkoxy group or an $—OSO_3^-$ group, $R_3$ represents the -T-Biot linkage or a $(C_1-C_6)$alkoxy group, $R_4$ represents the -T-Biot linkage, a $(C_1-C_6)$alkoxy group or an $—OSO_3^-$ group or else $R_4$ constitutes an $—O—CH_2—$ bridge, the $—CH_2—$ group being bonded to the carbon atom carrying the carboxyl functional group on the same ring;

it being understood that at least one of the $R_1$, $R_2$, $R_3$ or $R_4$ substituents represents a -T-Biot group, W represents an oxygen atom or a methylene group, T represents one of the linkages chosen from: NH

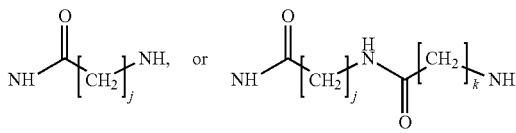

in which j and k, which are identical or different, are integers which can take any value from 1 to 10;

Biot represents the group:

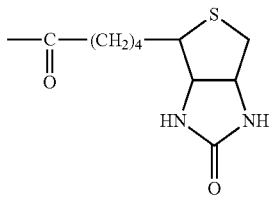

and their pharmaceutically acceptable salts.

As indicated above, it should be noted that, generally in the present description, a wavy line denotes a bond situated either below or above the plane of the pyranose ring.

The monosaccharides present in Po can be identical to or different from one another and the interglycoside bonds can be of the α or β type.

These monosaccharides are advantageously chosen from the D or L hexoses alose, altrose, glucose, mannose, galose, idose, galactose or talose (in this case, h=2) or from the D or L pentoses ribose, arabinose, xylose or lyxose (in this case, h=2). Other monosaccharides, such as, for example, deoxy sugars, can also be used (h=1 and/or —$CH_2R_1$=$CH_3$).

The polysaccharide part Po can be composed of 0 to 25 alkylated and di- or trisulphated monosaccharide units.

The polysaccharide part Po can also be composed of 0 to 25 alkylated and mono- or disulphated monosaccharide units.

The polysaccharide part Po can be composed of 0 to 25 uncharged and/or partially charged and/or completely charged alkylated monosaccharide units.

The charged or uncharged units can be dispersed along the chain or, on the other hand, they can be grouped into charged or uncharged saccharide domains.

The bonds between the units can be 1,2; 1,3; 1,4; 1,5; 1,6; and of the α or β type.

In the present description, the choice has been made to represent the $^1C_4$ conformation for L-iduronic acid and the $^4C_1$ conformation for D-glucuronic acid but it is well known that, generally, the conformation in solution of monosaccharide units fluctuates.

Thus, L-iduronic acid can have the $^1C_4$, $^2S_0$ or $^4C_1$ conformation.

According to one of its aspects, the invention relates to the polysaccharides of formula (I.1):

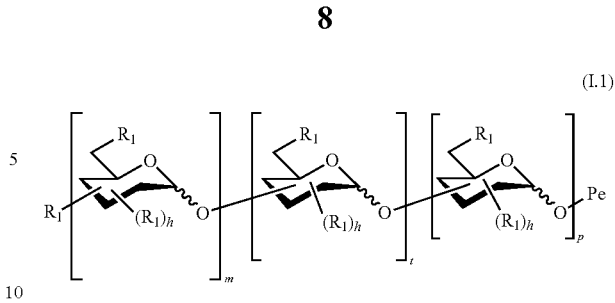

(I.1)

in which:

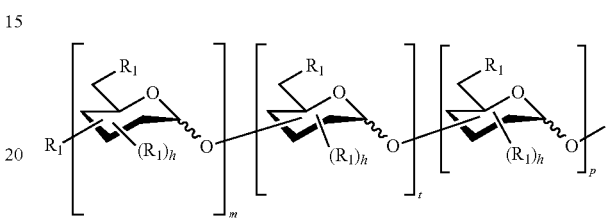

denotes a specific family of polysaccharides Po which are bonded via their anomeric carbon to Pe as defined for (I),

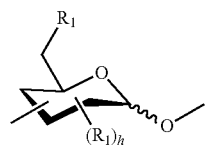

is as defined for (I), the $R_1$ groups are as defined for (I) and, for the same monosaccharide, can be identical or different, the monosaccharide present in [ ]$_m$ is repeated m times, the monosaccharide present in [ ]$_t$ is repeated t times and the monosaccharide present in [ ]$_p$ is repeated p times, m is an integer varying from 1 to 5, t is an integer varying from 0 to 24 and p is an integer varying from 0 to 24, it being understood that $1 \leq m+t+p \leq 25$, and their pharmaceutically acceptable salts.

Among these polysaccharides of formula (I.1), the polysaccharides in which only one of the $R_1$, $R_2$, $R_3$ or $R_4$ substituents represents the -T-Biot linkage with T and Biot being as defined for (I), and their pharmaceutically acceptable salts, constitute another aspect of the invention.

According to a specific aspect, the invention relates to the hexadecasaccharides of formula (I.2):

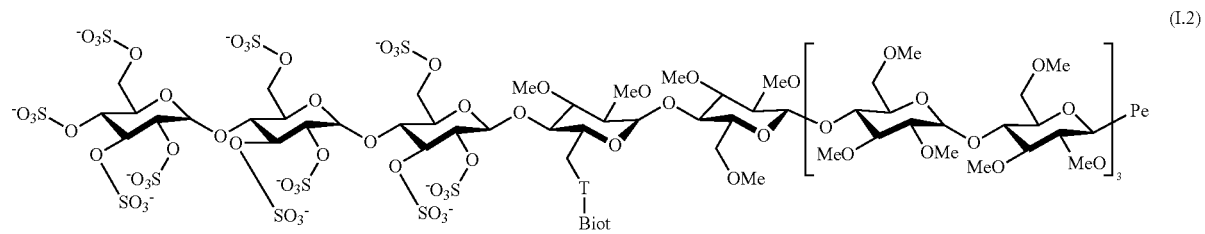

(I.2)

in which:

T represents one of the linkages chosen from: NH,

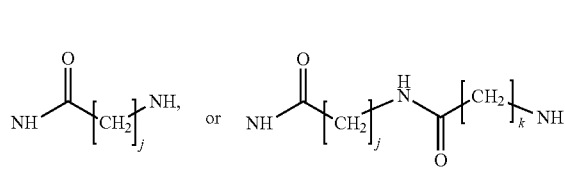

in which j and k, which are identical or different, are integers which can take any value from 1 to 10;

Biot represents the group:

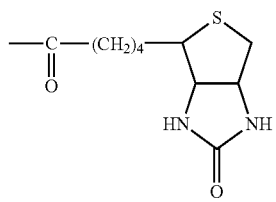

Pe represents a pentasaccharide of structure:

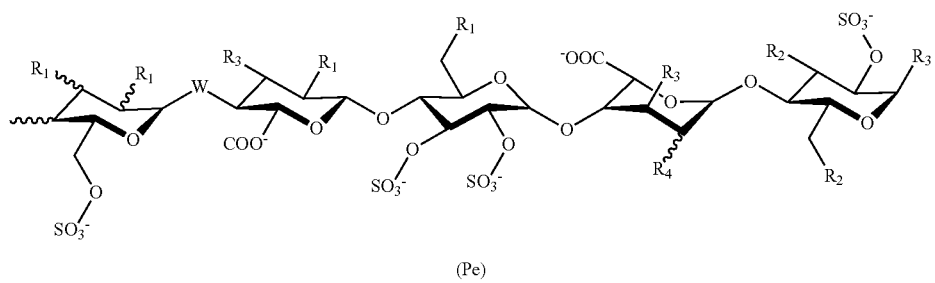

(Pe)

in which:
$R_1$ represents a $(C_1-C_6)$ alkoxy group or an $—OSO_3^-$ group,
$R_2$ represents a $(C_1-C_6)$ alkoxy group or an $—OSO_3^-$ group,
$R_3$ represents a $(C_1-C_6)$ alkoxy group,
$R_4$ represents a $(C_1-C_6)$ alkoxy group or an $—OSO_3^-$ group, or else $R_4$ constitutes an $—O—CH_2—$ bridge, the $—CH_2—$ group being bonded to the carbon atom carrying the carboxyl functional group on the same ring,
W represents an oxygen atom or a methylene group, and their pharmaceutically acceptable salts.

According to another of its aspects, the invention relates to the pentasaccharides of formula (I.3):

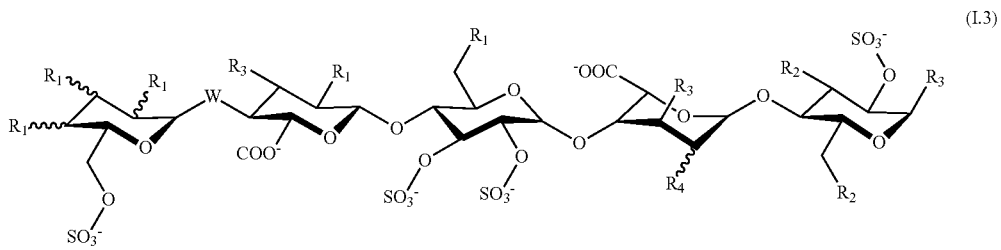

(I.3)

in which $R_1$, $R_2$, $R_3$, $R_4$ and W are as defined for (I), and their pharmaceutically acceptable salts.

Among these pentasaccharides of formula (I.3), the pentasaccharides in which only one of the $R_1$, $R_2$, $R_3$ or $R_4$ substituents represents the -T-Biot linkage with T and Biot being as defined for (I), and their pharmaceutically acceptable salts, constitute another aspect of the invention.

Among these pentasaccharides of formula (I.3), another subject-matter of the invention is the pentasaccharides of formula (I.4):

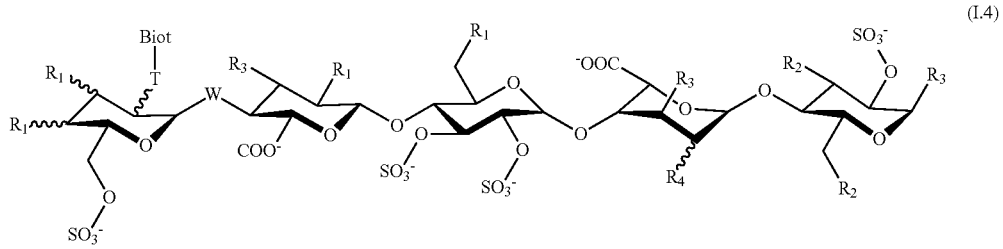
(I.4)

in which:

T represents one of the linkages chosen from: NH,

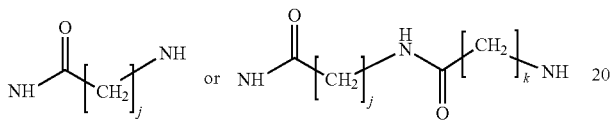

in which j and k, which are identical or different, are integers which can take any value from 1 to 10;

Biot represents the group:

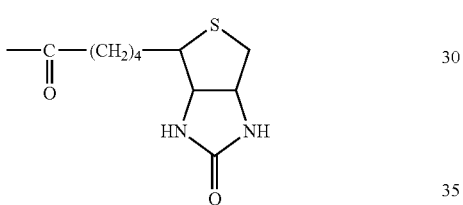

$R_1$ represents a $(C_1-C_6)$ alkoxy group or an —$OSO_3^-$ group, $R_2$ represents a $(C_1-C_6)$ alkoxy group or an —$OSO_3^-$ group, $R_3$ represents a $(C_1-C_6)$alkoxy group, $R_4$ represents a $(C_1-C_6)$alkoxy group or an —$OSO_3^-$ group, or else $R_4$ constitutes an —O—$CH_2$— bridge, the —$CH_2$— group being bonded to the carbon atom carrying the carboxyl functional group on the same ring, W represents an oxygen atom or a methylene group, and their pharmaceutically acceptable salts.

According to another of its aspects, the invention relates to the following polysaccharides:

Methyl(2,3,4,6-tetra-O-sulphonato-α-D-glucopyranosyl)-(1→4)-(2,3,6-tri-O-sulphonato-α-D-glucopyranosyl)-(1→4)-(2,3,6-tri-O-sulphonato-β-D-glucopyranosyl)-(1→4)-(6-biotinamido-6-deoxy-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-O-(2,3,6-tri-O-methyl-β-D-glucopyranosyl)-(1→4)]₃-(6-O-sulphonato-2,3-di-O-methyl-α-D-gluco-pyranosyl)-(1→4)-(2,3-di-O-methyl-β-D-glucopyrano-syluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt, Methyl(2,3,4,6-tetra-O-sulphonato-α-D-gluco-pyranosyl)-(1→4)-(2,3,6-tri-O-sulphonato-α-D-glucopyranosyl)-(1→4)-(2,3,6-tri-O-sulphonato-(3-D-glucopyranosyl)-(1→4)-(6-[6-(biotinamido)-hexamido]-6-deoxy-2,3-di-O-methyl-α-D-gluco-pyranosyl)-(1→4)-(2,3,6-tri-O-methyl-(3-D-gluco-pyranosyl)-(1→4)-[(2,3,6-tri-O-methyl-α-D-gluco-pyranosyl)-(1→4)-O-(2,3,6-tri-O-methyl-(3-D-gluco-pyranosyl)-(1→4)]₃-(6-O-sulphonato-2,3-di-O-methyl-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1-+4)-(2,3-di-O-methyl-α-L-idopyranosyluronic acid)-(1→4)-2,3,6-tri-O-sulphonato-α-D-glucopyranoside, sodium salt, Methyl(2,3,4,6-tetra-O-sulphonato-α-D-gluco-pyranosyl)-(1→4)-(2,3,6-tri-O-sulphonato-α-D-glucopyranosyl)-(1→4)-(2,3,6-tri-O-sulphonato-(3-D-glucopyranosyl)-(1→4)-(6-[6-(6-biotinamidohexamido)hexamido]-6-deoxy-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-O-(2,3,6-tri-O-methyl-β-D-glucopyranosyl)-(1→4)]₃-(6-O-sulphonato-2,3-di-O-methyl-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt, Methyl(2-biotinamido-2-deoxy-3,4-di-O-methyl-6-O-sulphonato-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-gluco-pyranoside, sodium salt, Methyl(2-[N-(6-biotinamidohexanoyl)]-2-deoxy-3,4-di-O-methyl-6-O-sulphonato-α-D-gluco-pyranosyl)-(1→4)-(2,3-di-O-methyl-β-D-gluco-pyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-O-sulphonato-α-D-glucopyranoside, sodium salt, Methyl(2-[6-(6-biotinamidohexamido)hexamido]-2-deoxy-3,4-di-O-methyl-6-O-sulphonato-α-D-glucopyranosyl)-(1→4)-(2,3-di-O-methyl-β-D-gluco-pyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt.

The invention encompasses the polysaccharides in their acid form or in the form of any one of their pharmaceutically acceptable salts. In the acid form, the —COO⁻ and —SO₃⁻ functional groups are respectively in the —COOH and —SO₃H forms.

The term "pharmaceutically acceptable salt of the polysaccharides of the invention" is understood to mean a polysaccharide in which one or more of the —COO⁻ and/or —SO₃⁻ functional groups are bonded ionically to a pharmaceutically acceptable cation. The preferred salts according to the invention are those for which the cation is chosen from the cations of alkali metals and more preferably still those for which the cation is Na⁺ or K⁺.

The compounds of the above formula (I) also comprise those in which one or more hydrogen or carbon atoms have been replaced by their radioactive isotope, for example tritium or carbon-14. Such labelled compounds are of use in research, metabolic or pharmacokinetic studies and in biochemical assays, as ligands.

The principle of the process for the preparation of the compounds according to the invention involves the use of di- or oligosaccharide base synthons prepared as reported above in the literature. Reference will in particular be made to Patents or Patent Applications EP 300 099, EP 529 715, EP 621 282 and EP 649 854 and to the documents C. van Boeckel, M. Petitou, *Angew. Chem. Int. Ed. Engl.*, 1993, 32, 1671-1690. These synthons are subsequently coupled to one another so as to provide a fully protected equivalent of a polysaccharide according to the invention. This protected equivalent is subsequently converted into a compound according to the invention.

One of the base synthons mentioned above comprises a specific protected functional group making possible the subsequent introduction of biotin or a biotin derivative, for example a latent amine functional group in the form of the azido group or protected in the form of the N-phthalimido group.

In the coupling reactions mentioned above, a "donor" di- or oligosaccharide, activated on its anomeric carbon, reacts with an "acceptor" di- or oligosaccharide having a free hydroxyl.

The present invention relates to a process for the preparation of the compounds of formula (I), characterized in that: in a first stage, a fully protected equivalent of the desired polysaccharide (I), comprising a protected precursor of the Pe domain extended at its nonreducing end by a protected precursor of the sulphated polysaccharide Po, is synthesized, one of these precursors comprising in particular a suitably protected amine functional group for the subsequent introduction of biotin or a biotin derivative; in a second stage, the negatively charged groups are introduced and/or unmasked; in a third stage, the amine functional group is deprotected and then biotin or the biotin derivative is introduced.

The synthesis of Pe is carried out according to the methods described in particular in the patent applications published under the numbers WO 98/03554 and WO 99/36443 and in the literature (cited above).

The polysaccharide part which is the precursor of Po is synthesized according to reactions well known to a person skilled in the art using the methods for the synthesis of oligosaccharides (G. J. Boons, *Tetrahedron*, 1996, 52, 1095-1121, WO 98/03554 and WO 99/36443) or an oligosaccharide when an oligosaccharide which is a glycoside bond donor is coupled with an oligosaccharide which is a glycoside bond acceptor to result in another oligosaccharide, the size of which is equal to the sum of the sizes of the two reactive species. This sequence is repeated until the desired compound of formula (I) is obtained. The nature and the profile of the charge of the final compound desired determine the nature of the chemical entities used in the various stages of the synthesis, according to rules well known to a person skilled in the art. Reference may be made, for example, to C. van Boeckel and M. Petitou, *Angew. Chem. Int. Ed. Engl.*, 1993, 32, 1671-1690, or to H. Paulsen, "Advances in selective chemical syntheses of complex oligosaccharides", *Angew. Chem. Int. Ed. Engl.*, 21, 155-173 (1982).

The compounds of the invention are obtained from their fully protected polysaccharide precursors by using the following series of reactions:
- the alcohol functional groups which have to be converted into an O-sulpho group and the carboxylic acids are deprotected by removing the protective groups used during the preparation of the backbone, then,
- the sulpho groups are subsequently introduced,
- the amine functional group which makes possible the introduction of biotin or the biotin derivative is deprotected,
- biotin or the biotin derivative is introduced by a conventional amino acid coupling reaction.

The compounds of the invention can naturally be prepared by using various strategies known to a person skilled in the art for the synthesis of oligosaccharides.

The process described above is the preferred process of the invention. However, the compounds of formula (I) can be prepared by other methods well known in the chemistry of sugars, described, for example, in Monosaccharides, their chemistry and their roles in natural products, P. M. Collins and R. J. Ferrier, J. Wiley & Sons, 1995, and in G. J. Boons, *Tetrahedron*, 1996, 52, 1095-1121.

The pentasaccharides Pe can thus be obtained from disaccharide synthons in the way described in the publication by C. van Boeckel and M. Petitou, *Angew. Chem. Int. Ed. Engl.*, 1993, 32, 1671-1690.

The protective groups used in the process for the preparation of the compounds (I) are those commonly used in the chemistry of sugars, for example in Protective Groups in Organic Synthesis, T. W. Greene, John Wiley & Sons, New York, 1981.

The protective groups are advantageously chosen, for example, from the acetyl, halomethyl, benzoyl, levulinyl, benzyl, substituted benzyl, optionally substituted trityl, tetrahydropyranyl, allyl, pentenyl, tert-butyldimethylsilyl (tBDMS) or trimethylsilylethyl groups.

The activating groups are those conventionally used in the chemistry of sugars according to, for example, G. J. Boons, *Tetrahedron*, 1996, 52, 1095-1121. These activating groups are chosen, for example, from imidates, thioglycosides, pentenylglycosides, xanthates, phosphites or halides.

As regards the way in which biotin is bonded to the oligosaccharide and the nature of the biotin derivative, the chemical literature offers other possibilities which can be made use of by sets of protective groups well known to a person skilled in the art. Use will preferably be made of an amine functional group, or a thiol functional group, or a carboxylic acid functional group, or an aldehyde functional group, which will be reacted with a biotin derivative comprising a reactive group of the activated ester, maleimide, iodoacetyl or primary amine type, the reaction taking place according to the conditions described in the literature (cf. Savage et al., *Avidin-Biotin Chemistry: A Handbook*; Pierce Chemical Company, 1992).

The process described above makes it possible to obtain the compounds of the invention in the form of salts. To obtain the corresponding acids, the compounds of the invention in the form of salts are brought into contact with a cation-exchange resin in the acid form.

The compounds of the invention in the form of acids can subsequently be neutralized with a base to obtain the desired salt. Any inorganic or organic base which gives pharmaceutically acceptable salts with the compounds of formula (I) can be used for the preparation of the salts of the compounds of formula (I). Sodium hydroxide, potassium hydroxide, calcium hydroxide or magnesium hydroxide is preferably used as base. The sodium and calcium salts of the compounds of formula (I) are the preferred salts.

The compounds according to the invention have formed the subject of biochemical and pharmacological studies.

The overall antithrombotic activity of these products and their neutralization has been studied in a venous thrombosis model composed of an injection of tissue factor, followed by a stasis of the vena cava of rats, as described by J.-M. Herbert et al., *Blood*, 1998, 91, 4197-4205. In this model, inhibition of 60% of the thrombosis is obtained after intravenous injection of 0.1 to 30 mmol/kg of the compounds. The injection of avidin in a molar ratio of 1 to 1 000 greatly reduces the antithrombotic effect of these compounds, it being possible for the reduction obtained to be greater than 50%. In the same way, the prohaemorrhagic activity of the compounds is neutralized by injection of avidin at the abovementioned doses. Likewise, the circulating activity of the oligosaccharides, measured by the anti-Xa activity and/or the anti-IIa activity, is neutralized by injection of avidin.

Thus, another subject-matter of the present invention is a process employing avidin or streptavidin, characterized in that it makes it possible to neutralize the polysaccharides according to the invention. Avidin or streptavidin can be used for the preparation of medicaments intended to neutralize the polysaccharides according to the present invention.

By virtue of their biochemical and pharmacological activity, the oligosaccharides of the present invention constitute highly advantageous medicaments. Their toxicity is entirely compatible with this use. They are also very stable and are thus particularly suitable for constituting the active principle of patented pharmaceutical products.

They can be used in various pathologies resulting from a modification of the homeostasis of the coagulation system appearing in particular during disorders of the cardiovascular and cerebrovascular system, such as thromboembolic disorders associated with atherosclerosis and diabetes, for example unstable angina, apoplexy, postangioplasty restenosis, endarterectomy or the insertion of endovascular prostheses; or thromboembolic disorders associated with post-thrombolysis rethrombosis, with infarction, with dementia of ischaemic origin, with peripheral arterial diseases, with haemodialysis or with auricular fibrillations, or during the use of vascular prostheses for aortocoronary bypasses. Furthermore, these products can be used for the treatment or prevention of thrombo-embolic pathologies of venous origin, such as pulmonary embolisms. They can be used to prevent or treat the thrombotic complications observed, for example, following surgical operations, the growth of tumours or disturbances to coagulation induced by bacterial, viral or enzymatic activators. In the case of their use during the insertion of prostheses, the compounds of the present invention can cover prostheses and thus render them haemocompatible. In particular, they can be attached to intravascular prostheses (stents). In this case, they can optionally be modified chemically by introduction at the nonreducing or reducing end of an appropriate arm, as disclosed according to EP 649 854.

The compounds of the present invention can also be used as adjuvants during endarterectomy carried out with porous balloons.

The compounds according to the invention can be used in the preparation of medicaments intended for the treatment of the above diseases.

According to another of its aspects, a subject-matter of the present invention is thus a pharmaceutical composition comprising, as active principle, a synthetic polysaccharide according to the invention or one of its pharmaceutically acceptable salts, optionally in combination with one or more inert and appropriate excipients.

The said excipients are chosen according to the desired pharmaceutical form and the desired administration method: oral, sublingual, subcutaneous, intramuscular, intravenous, transdermal, transmucosal, local or rectal.

The active principle can also be presented in the form of a complex with a cyclodextrin, for example $\alpha$-, $\beta$- or $\gamma$-cyclodextrin, 2-hydroxypropyl-$\beta$-cyclodextrin or methyl-$\beta$-cyclodextrin.

The active principle can also be released by a balloon comprising it or by an endovascular expander introduced into the blood vessels. The pharmacological effectiveness of the active principle is thus unaffected.

In each dosage unit, the active principle is present in the amounts suited to the daily doses envisaged in order to obtain the desired prophylactic or therapeutic effect. Each dosage unit can comprise from 0.1 to 100 mg of active principle, preferably 0.5 to 50 mg. These doses of anticoagulant compounds might be neutralized by doses of avidin or streptavidin ranging from 1 to 1 000 mg by iv (intravenous) injection, bolus or infusion.

The compounds according to the invention can also be used in combination with one or more other active principles of use in the desired therapy, such as, for example, antithrombotics, anticoagulants, platelet aggregation inhibitors, such as, for example, dipyridamole, aspirin, ticlopidine or clopidogrel, or glycoprotein IIb/IIIa complex antagonists.

The following methods, preparations and schemes illustrate the synthesis of the various intermediates of use in the preparation of the polysaccharides according to the invention.

The following abbreviations are used: Bn: benzyl; Bz: benzoyl; TLC: thin layer chromatography; Ts: tosyl; Lev: levulinyl; Et: ethyl; Ph: phenyl; Me: methyl; Ac: acetyl; SE: trimethylsilylethyl; ESI: electron spray ionization; Biotin: hexahydro-2-oxo-1H-thieno[3,4-d]imidazole-4-pentanoic acid; Z: benzyloxycarbonyl.

Subsequently, examples of the synthesis of the compounds of the invention are described in detail by way of illustration.

SCHEME 1 - synthesis of the trisaccharide 9

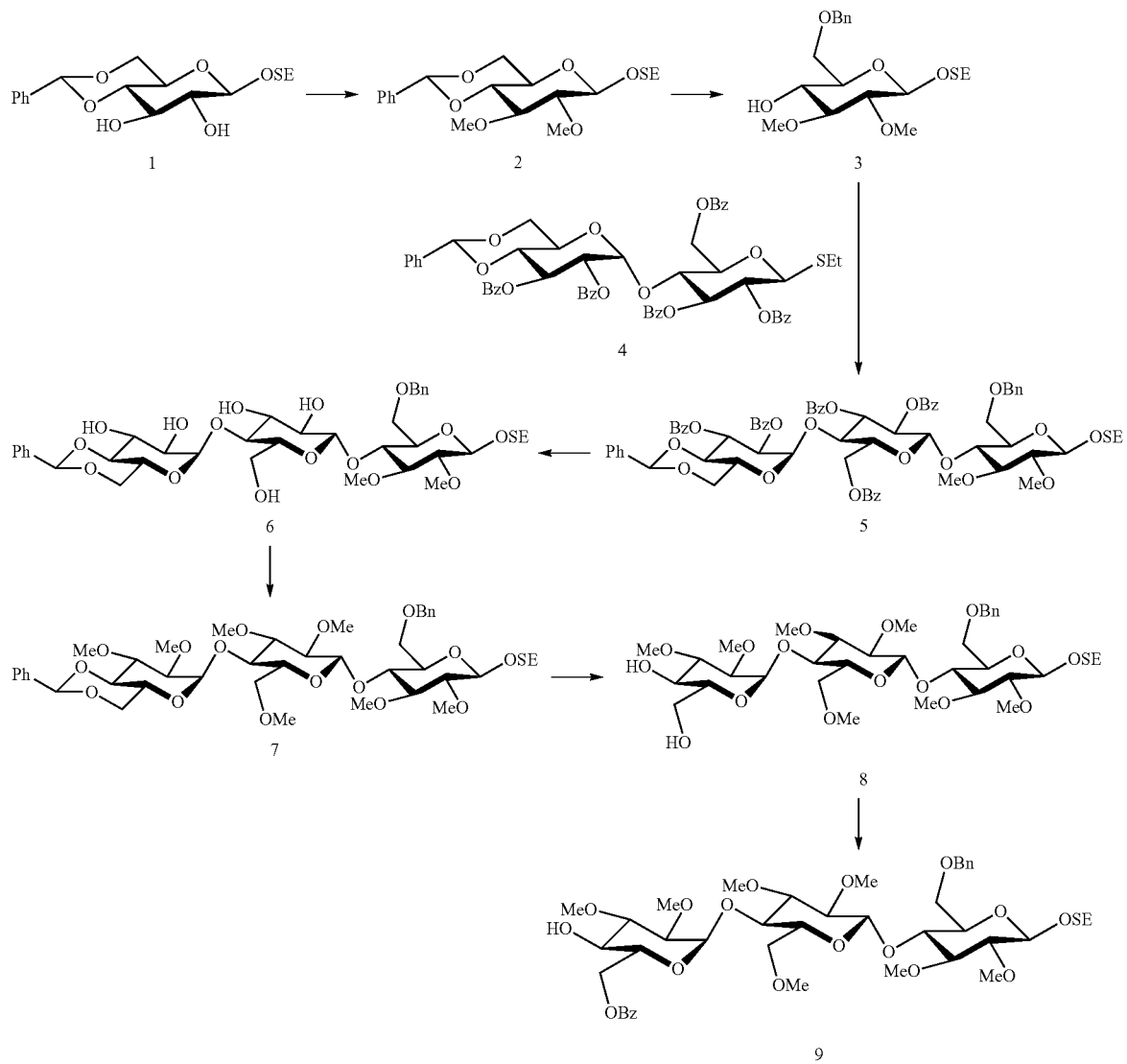

PREPARATION 1

2-(Trimethylsilyl)ethyl4,6-O-benzylidene-2,3-di-O-methyl-β-D-glucopyranoside(2)

Sodium hydride (18 g) is added portionwise at 0° C. to a solution of the compound 1 (15.8 g, 42.8 mmol) (prepared according to K. Jansson et al., *J. Org. Chem.*, 1988, 53, 5629-5647) and of methyl iodide (20 ml, 319 mmol) in tetrahydrofuran (350 ml). The reaction mixture is stirred for 4 hours at ambient temperature. The excess sodium hydride is destroyed with methanol and the reaction mixture is poured into ice-cold water (1.5 l). After extracting with ethyl acetate, the organic phase is washed with a saturated sodium chloride solution and water, dried over sodium sulphate and then concentrated under vacuum. The residue is purified by chromatography on a column of silica gel (15/1 (v/v) cyclohexane/ethyl acetate) to give 16.8 g of the compound 2.

$[\alpha]_D = -41°$ (c=0.69, dichloromethane).

PREPARATION 2

2-(Trimethylsilyl)ethyl6-O-benzyl-2,3-di-O-methyl-β-D-glucopyranoside (3)

3 Å molecular sieve powder (82 g), methyl orange (coloured indicator), sodium cyanoborohydride (34 g, 526 mmol) and then, dropwise, a saturated solution of hydrochloric acid in diethyl ether are successively added to a solution of the compound 2 (16 g, 40.3 mmol) in tetrahydrofuran (600 ml), until a pink colouring is obtained. After filtering and extracting with ethyl acetate, the organic phase is washed with a saturated sodium hydrogencarbonate solution and water, dried over sodium sulphate and then concentrated under vacuum. Chromatography on a column of silica gel (3/1 (v/v) toluene/ethyl acetate) makes it possible to obtain 12.5 g of the compound 3.

$[\alpha]_D = -42°$ (c=1.2, dichloromethane).

PREPARATION 3

2-(Trimethylsilyl)ethyl(2,3-di-O-benzoyl-4,6-O-benzylidene-α-D-glucopyranosyl)-(1→4)-(2,3,6-tri-O-benzoyl-β-D-glucopyranosyl)-(1→4)-6-O-benzyl-2,3-di-O-methyl-β-D-glucopyranoside (5)

A mixture of thioglycoside 4 (16.52 g, 16.60 mmol) (obtained according to Preparation 1 of the patent application published under the number WO 99/36443), of the compound 3 (6.0 g, 15.05 mmol) and of 4 Å molecular sieve powder (16.7 g) in toluene (300 ml) is stirred under an argon atmosphere for 1 hour. The mixture is then cooled to −20° C. A solution of N-iodosuccinimide (3.9 g, 17.4 mmol) and of tri-fluoromethanesulphonic acid (0.17 ml, 1.97 mmol) in a 1/1 (v/v) dichloromethane/dioxane mixture (86 ml) is added dropwise to the reaction mixture. After 10 minutes, the reaction mixture is filtered, diluted with dichloromethane, washed excessively with a 1M sodium thiosulphate solution, a 10% sodium hydrogencarbonate solution and water, dried over sodium sulphate and then concentrated under vacuum. The residue is purified by chromatography on a column of silica gel (6/1 (v/v) toluene/ethyl acetate) to give 18.8 g of the trisaccharide 5.

$[\alpha]_D$=+ 34° (c=1.26, dichloromethane).

PREPARATION 4

2-(Trimethylsilyl)ethyl(4,6-O-benzylidene-α-D-glucopyranosyl)-(1→4)-(6-D-glucopyranosyl)-(1→4)-6-O-benzyl-2,3-di-O-methyl-β-D-glucopyranoside (6)

Potassium tert-butoxide (3.15 g) is added to a solution of the compound 5 (18.7 g, 14 mmol) in a 1/1 (v/v) methanol/dioxane mixture (140 ml). The reaction mixture is stirred for 2 hours at ambient temperature. It is neutralized with Dowex® 50WX4 H+ resin, filtered and concentrated under vacuum. The residue is purified by chromatography on a column of silica gel (20/1 (v/v) dichloromethane/methanol) to give 10.0 g of the compound 6.

$[\alpha]_D$=+29° (c=1.11, dichloromethane).

PREPARATION 5

2-(Trimethylsilyl)ethyl(4,6-O-benzylidene-2,3-di-O-methyl-α-D-glucopyranosyl)-(1→4)-(2,3,6-tri-O-methyl-β-D-glucopyranosyl)-(1→4)-6-O-benzyl-2,3-di-O-methyl-β-D-glucopyranoside (7)

Sodium hydride (5.2 g, 216 mmol) is added portionwise under an argon atmosphere to a cooled mixture (0° C.) of the compound 6 (9.93 g, 12.24 mmol) and of methyl iodide (9.0 ml, 138 mmol) in anhydrous tetrahydrofuran (100 ml). The mixture is stirred for 20 hours at ambient temperature. The excess sodium hydride is destroyed with methanol and the reaction mixture is poured into ice-cold water (500 ml). After extracting with ethyl acetate, the organic phase is washed with a saturated sodium chloride solution, dried over sodium sulphate and then concentrated under vacuum to give 11 g of the compound 7, which is used in the following stage without purification.

TLC: $R_f$=0.38, silica gel, 3/2 (v/v) toluene/ethyl acetate.

PREPARATION 6

2-(Trimethylsilyl)ethyl(2,3-di-O-methyl-α-D-glucopyranosyl)-(1→4)-(2,3,6-tri-O-methyl-β-D-glucopyranosyl)-(1→4)-6-O-benzyl-2,3-di-O-methyl-β-D-gluco-pyranoside (8)

The compound 7 (11 g) is dissolved in 60% acetic acid (180 ml) and stirred for 1 hour 30 at 80° C. The mixture is concentrated and coevaporated with toluene. The residue is purified by chromatography on a column of silica gel (2/1 (v/v) toluene/acetone) to give 8.46 g of the compound 8.

TLC: $R_f$=0.36, silica gel, 1/1 (v/v) toluene/acetone.

PREPARATION 7

2-(Trimethylsilyl)ethyl(6-O-benzoyl-2,3-di-O-methyl-α-D-glucopyranosyl)-(1→4)-(2,3,6-tri-O-methyl-β-D-gluco-pyranosyl)-(1→4)-6-O-benzyl-2,3-di-O-methyl-β-D-gluco-pyranoside (9)

1-Benzoyloxy-1H-benzotriazole (5.36 g, 22.4 mmol) and triethylamine (3.32 ml) are added to a solution of the compound 8 (8.41 g, 10.6 mmol) in dichloromethane (110 ml). The mixture is stirred for 20 hours at ambient temperature and then diluted with dichloromethane, washed with a saturated sodium hydrogencarbonate solution and water, dried over sodium sulphate and then concentrated under vacuum. The residue is purified by chromatography on a column of silica gel (5/0.5/0.25 (v/v/v) cyclohexane/ethyl acetate/ethanol) to give 8.40 g of the compound 9.

$[\alpha]_D$=+15° (c=2, dichloromethane).

SCHEME 2 - Synthesis of the pentasaccharide 14

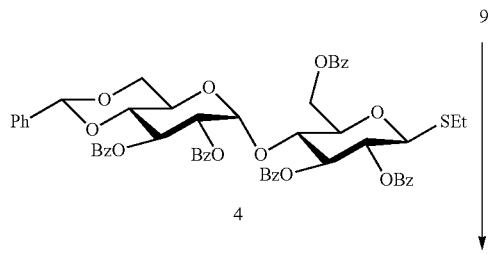

4

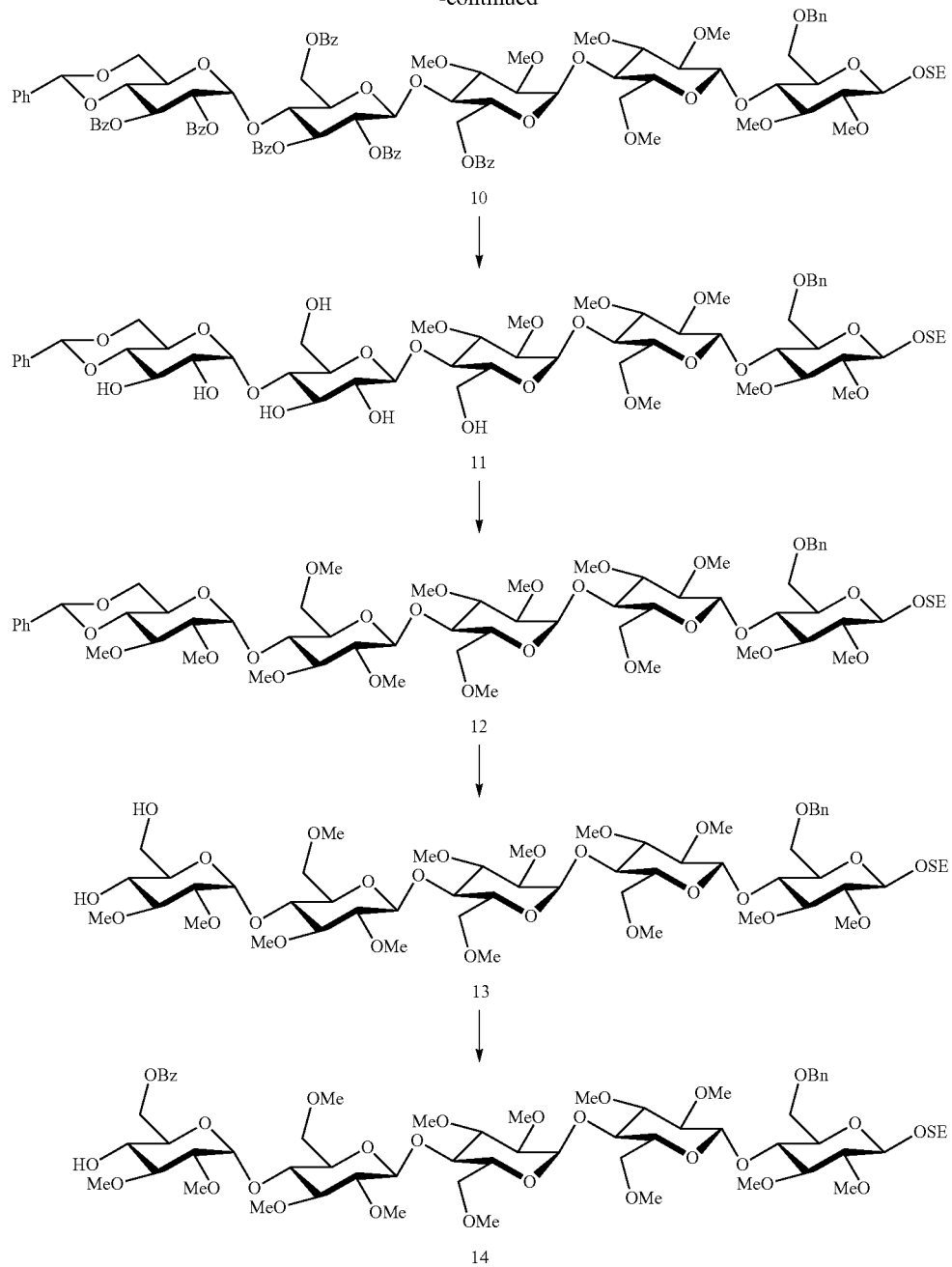

PREPARATION 8

2-(Trimethylsilyl)ethyl(2,3-di-O-benzoyl-4,6-O-benzylidene-α-D-glucopyranosyl)-(1→4)-(2,3,6-tri-O-benzoyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-6-O-benzoyl-2,3-di-O-methyl-β-D-glucopyranoside (10)

The compound 9 is converted into compound 10 according to the procedure described in PREPARATION 3.

$[\alpha]_D = +42°$ (c=2, dichloromethane).

PREPARATION 9

2-(Trimethylsilyl)ethyl(4,6-O-benzylidene-α-D-gluco-pyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-(1→4)-6-O-benzyl-2,3-di-O-methyl-β-D-glucopyranoside (11)

The compound 10 is converted into compound 11 according to the procedure described in PREPARATION 4.

TLC: $R_f$=0.35, silica gel, 10/1 (v/v) dichloro-methane/methanol.

PREPARATION 10

2-(Trimethylsilyl)ethyl(4,6-O-benzylidene-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-(1→4)-6-O-benzyl-2,3-di-O-methyl-β-D-glucopyranoside (12)

The compound 11 is converted into compound 12 according to the procedure described in PREPARATION 5.
TLC: $R_f$=0.11, silica gel, 1/2 (v/v) cyclohexane/ethyl acetate.

PREPARATION 11

2-(Trimethylsilyl)ethyl(2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-(1→4)-6-O-benzyl-2,3-di-O-methyl-β-D-glucopyranoside (13)

The compound 12 is converted into compound 13 according to the procedure described in PREPARATION 6.

TLC: $R_f$=0.33, silica gel, 2/0.5/0.5 (v/v/v) cyclo-hexane/ethyl acetate/ethanol.

PREPARATION 12

2-(Trimethylsilyl)ethyl(6-O-benzoyl-2,3-di-O-methyl-α-D-glucopyranosyl)-(1→4)-(2,3,6-tri-O-methyl-β-D-gluco-pyranosyl)-(1→4)-(2,3,6-tri-O-methyl-α-D-gluco-pyranosyl)-(1→4)-(2,3,6-tri-O-methyl-β-D-gluco-pyranosyl)-(1→4)-6-O-benzyl-2,3-di-O-methyl-β-D-gluco-pyranoside (14)

The compound 13 is converted into compound 14 according to the procedure described in PREPARATION 7.

TLC: $R_f$=0.16, silica gel, 3/0.5/0.5 (v/v/v) cyclo-hexane/ethyl acetate/ethanol.

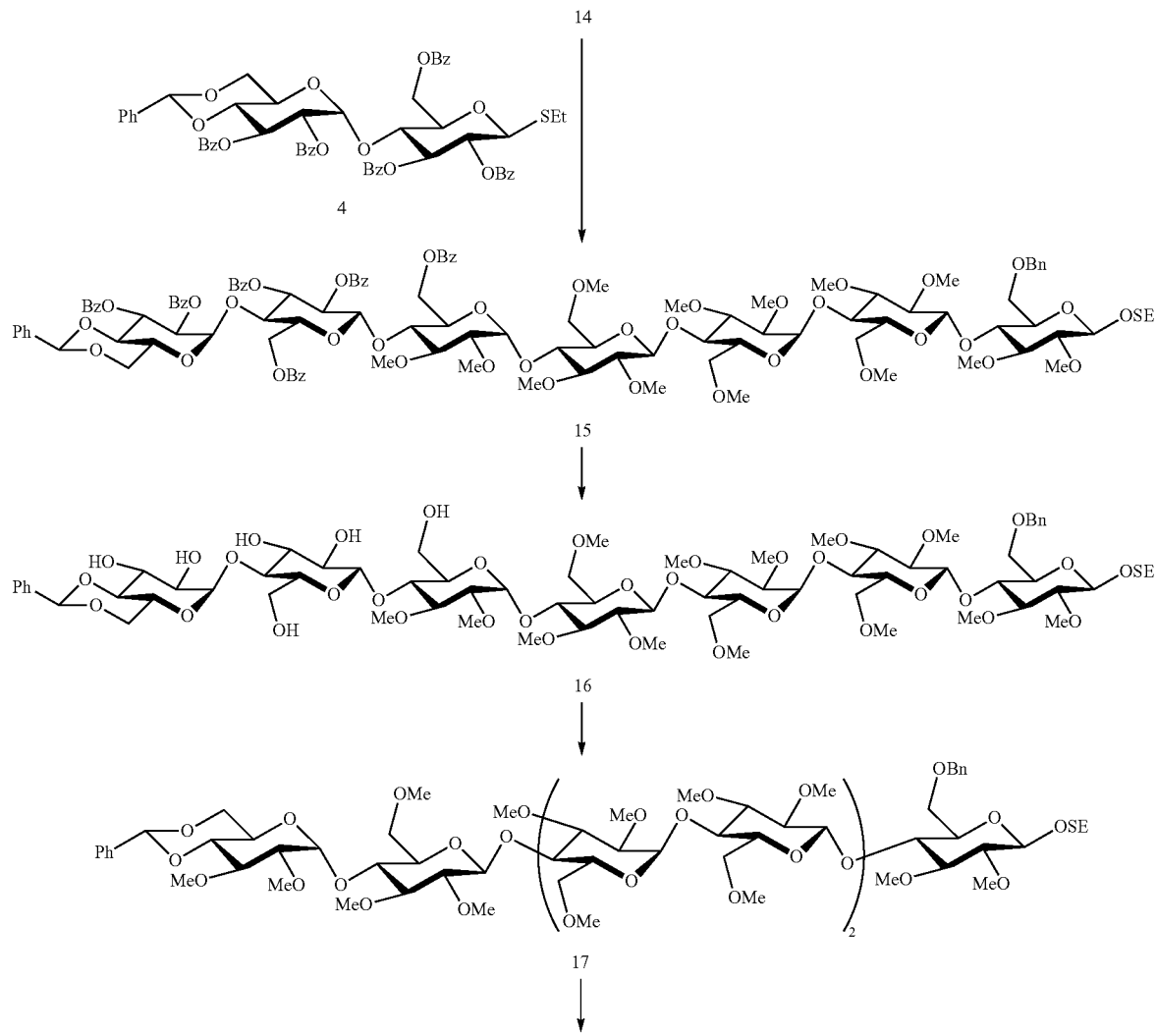

SCHEME 3 - Synthesis of the heptasaccharide 19

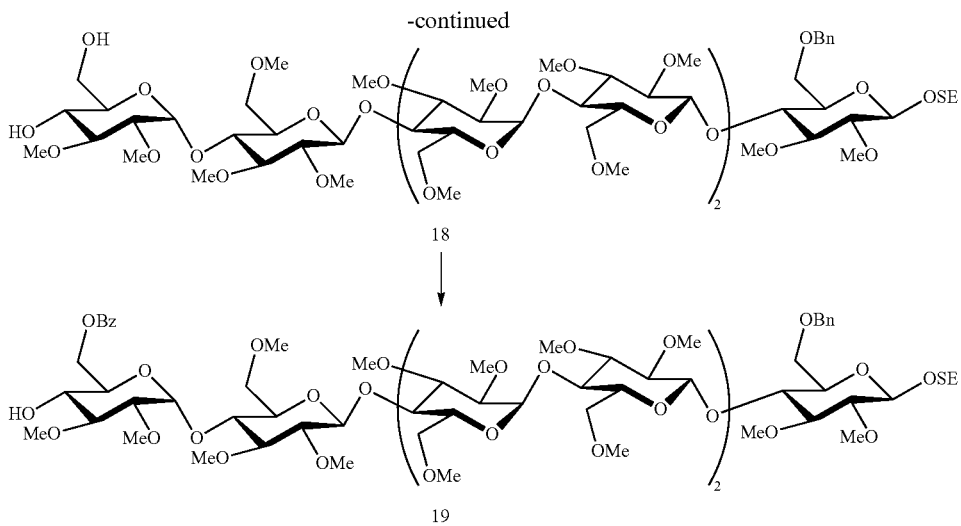

PREPARATION 13

2-(Trimethylsilyl)ethyl(2,3-di-O-benzoyl-4,6-O-benzylidene-α-D-glucopyranosyl)-(1→4)-(2,3,6-tri-O-benzoyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-(1→4)-6-O-benzyl-2,3-di-O-methyl-β-D-glucopyranoside (15)

The reaction of coupling the compound 14 with the disaccharide 4 is carried out according to the procedure described in PREPARATION 3 to provide the compound 15.
[α]$_D$=+52° (c=1.1, dichloromethane).

PREPARATION 14

2-(Trimethylsilyl)ethyl(4,6-O-benzylidene-α-D-gluco-pyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-(1→4)-(2,3,6-tri-O-methyl-α-D-gluco-pyranosyl)-(1→4)-(2,3,6-tri-O-methyl-β-D-gluco-pyranosyl)-(1→4)-6-O-benzyl-2,3-di-O-methyl-β-D-glucopyranoside (16)

The compound 15 is converted into compound 16 according to the procedure described in PREPARATION 4.
TLC: R$_f$=0.31, silica gel, 10/1 (v/v) dichloro-methane/methanol.

PREPARATION 15

2-(Trimethylsilyl)ethyl(4,6-O-benzylidene-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-gluco-pyranosyl)-(1→4)]$_2$-6-O-benzyl-2,3-di-O-methyl-β-D-glucopyranoside (17)

The compound 16 is converted into compound 17 according to the procedure described in PREPARATION 5.

TLC: R$_f$=0.46, silica gel, 10/1 (v/v) dichloro-methane/methanol.

PREPARATION 16

2-(Trimethylsilyl)ethyl(2,3-di-O-methyl-α-D-gluco-pyranosyl)-(1→4)-(2,3,6-tri-O-methyl-β-D-gluco-pyranosyl)-(1→4)-(2,3,6-tri-O-methyl-α-D-gluco-pyranosyl)-(1→4)-(2,3,6-tri-O-methyl-β-D-gluco-pyranosyl)-(1→4)-(2,3,6-tri-O-methyl-α-D-glucopyranosyl)-(1→4)-(2,3,6-tri-O-methyl-β-D-gluco-pyranosyl)-(1→4)-6-O-benzyl-2,3-di-O-methyl-β-D-glucopyranoside (18)

The compound 17 is converted into compound 18 according to the procedure described in PREPARATION 6.

TLC: R$_f$=0.42, silica gel, 1/0.5/0.5 (v/v/v) cyclohexane/ethyl acetate/ethanol.

PREPARATION 17

2-(Trimethylsilyl)ethyl(6-O-benzoyl-2,3-di-O-methyl-α-D-glucopyranosyl)-(1→4)-(2,3,6-tri-O-methyl-β-D-glucopyranosyl)-(1→4)-(2,3,6-tri-O-methyl-α-D-gluco-pyranosyl)-(1→4)-(2,3,6-tri-O-methyl-β-D-gluco-pyranosyl)-(1→4)-(2,3,6-tri-O-methyl-α-D-gluco-pyranosyl)-(1→4)-(2,3,6-tri-O-methyl-β-D-gluco-pyranosyl)-(1→4)-6-O-benzyl-2,3-di-O-methyl-β-D-gluco-pyranoside (19)

The compound 18 is converted into compound 19 according to the procedure described in PREPARATION 7.

TLC: R$_f$=0.25, silica gel, 3/0.5/0.5 (v/v/v) cyclo-hexane/ethyl acetate/ethanol.

SCHEME 4 - Synthesis of the nonasaccharide 23

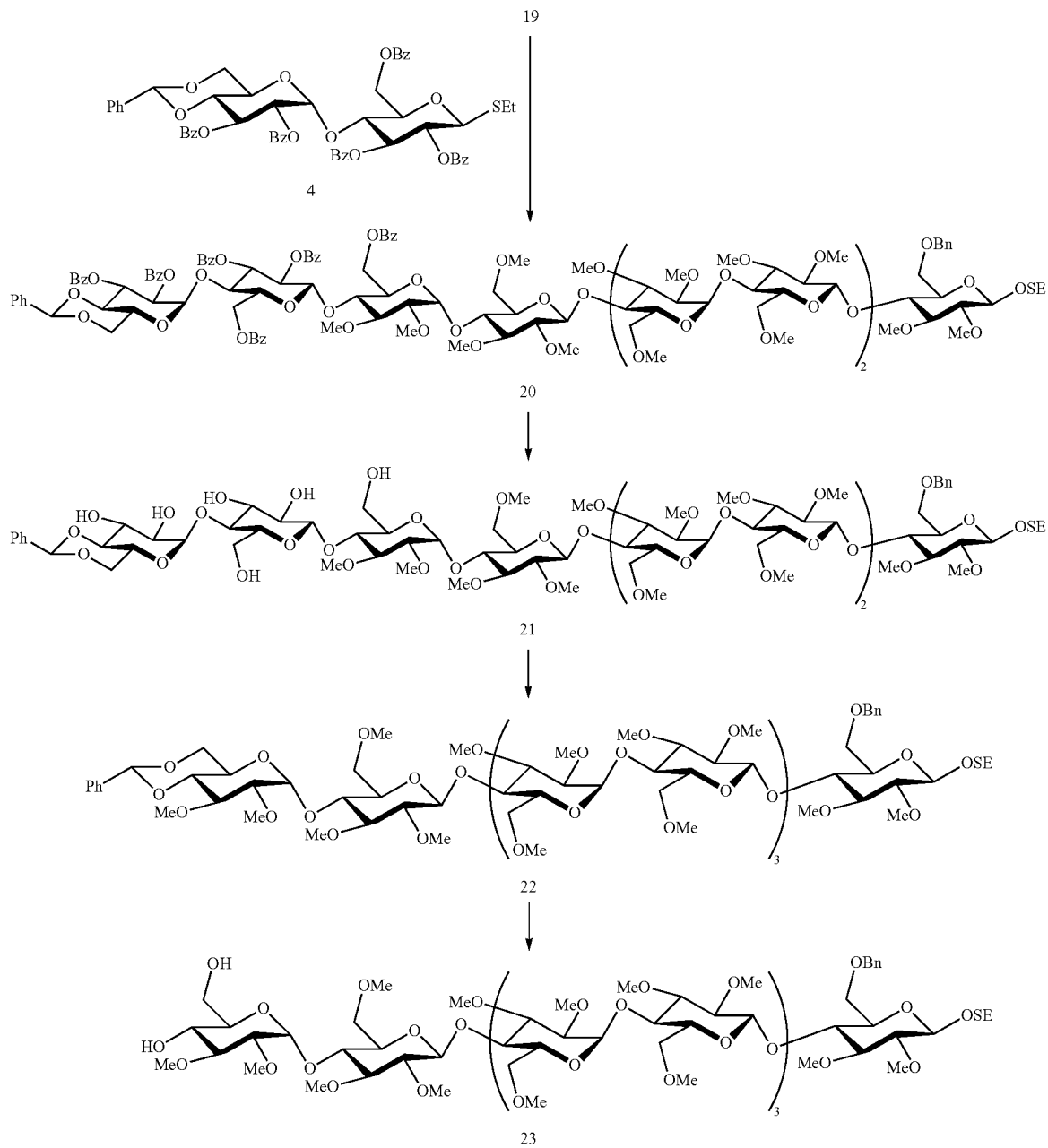

PREPARATION 18

2-(Trimethylsilyl)ethyl(2,3-di-O-benzoyl-4,6-O-benzylidene-α-D-glucopyranosyl)-(1→4)-(2,3,6-tri-O-benzoyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]$_2$-6-O-benzoyl-2,3-di-O-methyl-β-D-glucopyranoside (20)

A mixture of the thioglycoside 4 (5.2 g, 5.23 mmol), of heptasaccharide 19 (4.72 g, 2.75 mmol) and of 4 Å molecular sieve powder in toluene is stirred under an argon atmosphere for 1 hour. A solution of N-iodosuccinimide (1.36 g, 5.85 mmol) and of trifluoro-methanesulphonic acid (0.140 ml, 1.56 mmol) in 1/1 (v/v) dichloromethane/dioxane (32 ml) is then added dropwise at 0° C. After 15 minutes, the reaction mixture is filtered, diluted with dichloromethane, washed successively with a 1 M sodium thiosulphate solution, a 10% sodium hydrogencarbonate solution and water, dried over sodium sulphate and concentrated under vacuum. The residue is purified by chromatography on a column of silica gel (3/0.5/0.5 (v/v/v) cyclohexane/ethyl acetate/ethanol) to give 7.13 g of the compound 20.

$[\alpha]_D$=+65° (c=1.4, dichloromethane).

PREPARATION 19

2-(Trimethylsilyl)ethyl(4,6-O-benzylidene-α-D-glucopyranosyl)-(1→4)-β-D-glucopyranosyl)-(1→4)-(2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]$_2$-6-O-benzyl-2,3-di-O-methyl-β-D-glucopyranoside (21)

The compound 20 is converted into compound 21 according to the procedure described in PREPARATION 4.

TLC: $R_f$=0.27, silica gel, 10/1 (v/v) dichloromethane/methanol.

PREPARATION 20

2-(Trimethylsilyl)ethyl(4,6-O-benzylidene-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-(1→4)]$_3$-6-O-benzyl-2,3-di-O-methyl-β-D-glucopyranoside (22)

The compound 21 is converted into compound 22 according to the procedure described in PREPARATION 5.

TLC: $R_f$=0.31, silica gel, 5/1/1 (v/v/v) cyclohexane/ethyl acetate/ethanol.

PREPARATION 21

2-(Trimethylsilyl)ethyl(2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]$_3$-6-O-benzyl-2,3-di-O-methyl-β-D-glucopyranoside (23)

The compound 22 is converted into compound 23 according to the procedure described in PREPARATION 6.

TLC: $R_f$=0.35, silica gel, 2/1/1 (v/v/v) cyclohexane/ethyl acetate/ethanol.

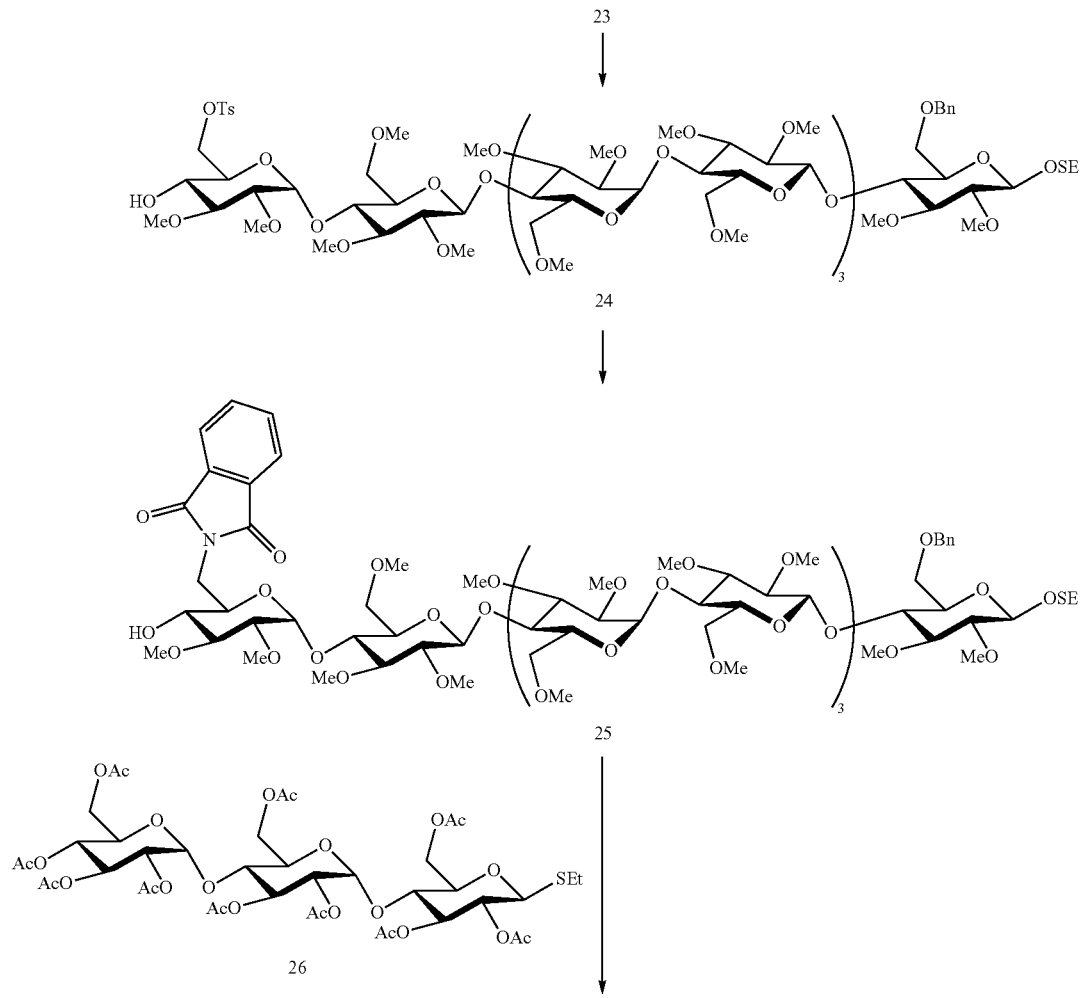

SCHEME 5 - Synthesis of the nonasaccharide 29

-continued

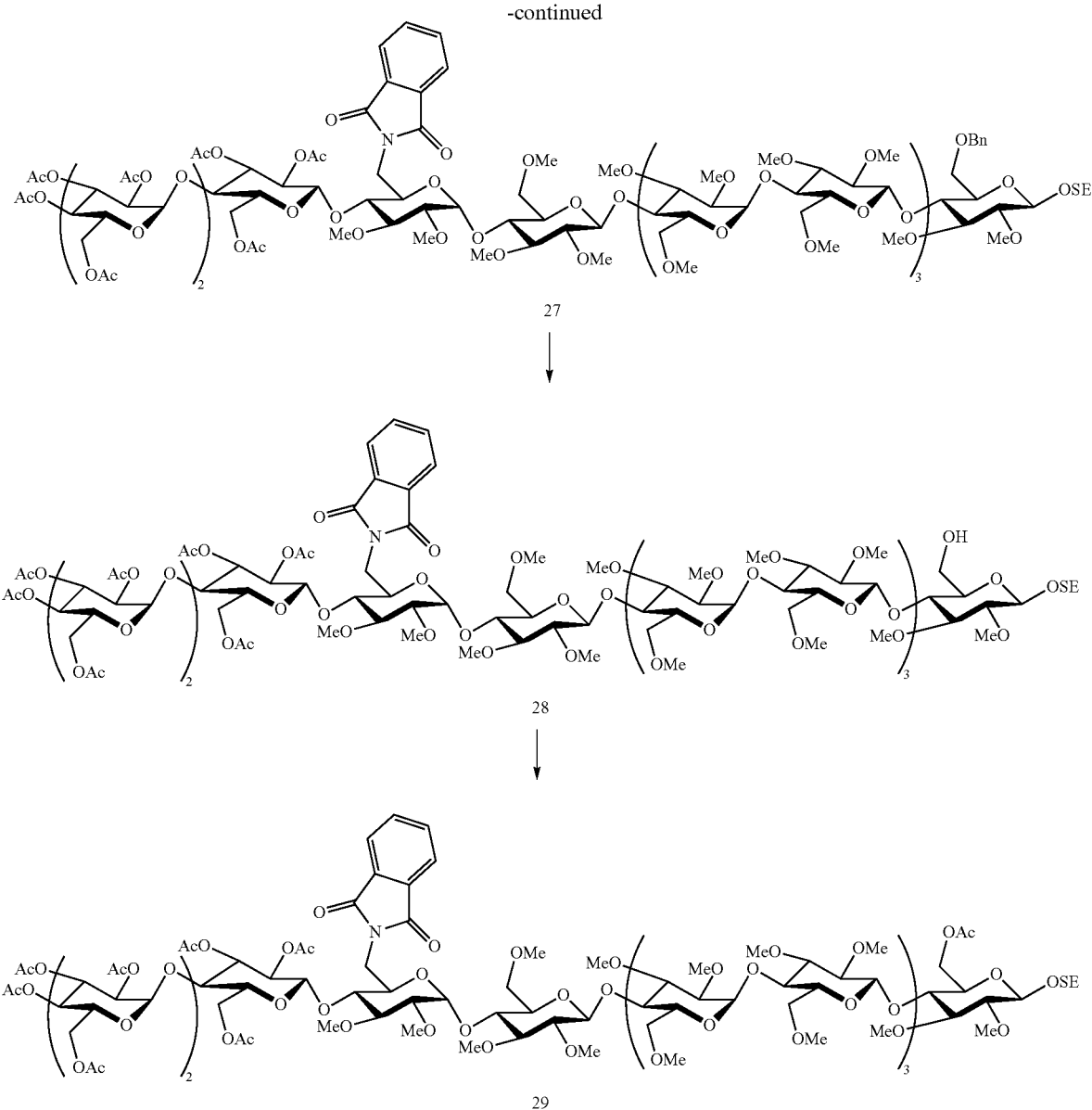

PREPARATION 22

2-(Trimethylsilyl)ethyl(2,3-di-O-methyl-6-O-tosyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-6-O-benzyl-2,3-di-O-methyl-β-D-glucopyranoside (24)

The compound 23 (1.09 g) is dissolved in pyridine (10 ml) under an argon atmosphere and then tosyl chloride (1.03 g) is added. After stirring for 2 hours, the reaction mixture is diluted with dichloromethane (100 ml). The organic phase is washed successively with a 10% potassium hydrogen sulphate solution and then water, dried and evaporated to dryness. After chromatography on a column of silica gel (2.3/2 (v/v) toluene/acetone), 1.77 g of the compound 24 are obtained.

TLC: $R_f$=0.5, silica gel, 3/1/1 (v/v/v) cyclohexane/ethyl acetate/ethanol.

PREPARATION 23

2-(Trimethylsilyl)ethyl(6-deoxy-2,3-di-O-methyl-6-phthalimido-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-6-O-benzyl-2,3-di-O-methyl-β-D-glucopyranoside (25)

Potassium phthalimide (225 mg, 1.38 mmol) and then 18-crown-6 crown ether (121.5 mg, 0.46 mmol) are added to a solution of the compound 24 (500 mg, 0.23 mmol) in anhydrous N,N-dimethylformamide (11 ml) comprising 4 Å molecular sieve powder. The mixture is stirred for 4 hours at 80° C. After having been cooled, the reaction mixture is diluted with dichloromethane, filtered through Celite and concentrated. The residue is purified by chromatography on Sephadex® LH20 gel (3×100 cm) (1/1 (v/v) dichloromethane/ethanol), followed by chromatography on a column of silica gel (11/2 (v/v) toluene/ethanol), to give 417.4 mg of the compound 25.

TLC: $R_f$=0.38, silica gel, 11/2 (v/v) toluene/ethanol.

PREPARATION 24

2-(Trimethylsilyl)ethyl(2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-deoxy-2,3-di-O-methyl-6-phthalimido-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-6-O-benzyl-2,3-di-O-methyl-β-D-glucopyranoside (27)

A mixture of thioglycoside 26 (1.515 g, 1.564 mmol) (prepared according to compound 41, Preparation 36 of Patent WO 99/36443), of the acceptor 25 (840 mg, 0.391 mmol) and of 4 Å molecular sieve powder (2.15 g) in toluene (33 ml) is stirred under an argon atmosphere for 1 hour. The reaction mixture is cooled to 0° C. and a solution of N-iodosuccinimide (387 mg) and of trifluoromethanesulphonic acid (55.4 μl) in 1/1 (v/v) dichloromethane/dioxane (7 ml) is introduced therein. After 10 minutes, the mixture is filtered, diluted with toluene, washed successively with a 1 M sodium thiosulphate solution, in a 10% sodium hydrogen carbonate solution and in water, dried over sodium sulphate and then concentrated under vacuum. The residue is purified by chromatography on Sephadex® LH20 gel (1/1 (v/v) dichloromethane/ethanol), followed by chromatography on a column of silica gel (5/4 (v/v) toluene/acetone), and results in 887 mg of the compound 27.

$[α]_D$=+70° (c=0.35, dichloromethane).

PREPARATION 25

2-(Trimethylsilyl)ethyl(2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-deoxy-2,3-di-O-methyl-6-phthalimido-α-D-glucopyranosyl)-(1-A)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-2,3-di-O-methyl-β-D-glucopyranoside (28)

A solution of the compound 27 (750 mg, 0.245 mmol) in acetic acid (37 ml) is treated under hydrogen pressure (5 bar) in the presence of 10% palladium-on-charcoal (750 mg) for 2 hours 30. After filtering, the solution is concentrated and the residue is purified by chromatography on a column of silica gel (6/1 (v/v) toluene/ethanol) to give 728 mg of the compound 28.

TLC: $R_f$=0.32, silica gel, 6/1 (v/v) toluene/ethanol.

PREPARATION 26

2-(Trimethylsilyl)ethyl(2,3,4,6-tetra-O-acetyl-α-D-glucopyranosyl)-(1→4)-(2,3,6-tri-O-acetyl-α-D-gluco-pyranosyl)-1-(2,3,6-tri-O-acetyl-β-D-glucopyranosyl)-(1→4)-(6-deoxy-2,3-di-O-methyl-6-phthal-imido-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-gluco-pyranosyl)-(1→4)]₃-6-O-acetyl-2,3-di-O-methyl-β-D-glucopyranoside (29)

Triethylamine (51.1 μl, 0.368 mmol), acetic anhydride (32.5 μl, 0.344 mmol) and dimethylamino-pyridine (6.0 mg, 0.049 mmol) are added to a solution of the compound 28 (728 mg, 0.245 mmol) in dichloro-methane (10 ml). After stirring for 1 hour, the reaction mixture is diluted with dichloromethane, washed successively with a 10% potassium hydrogen sulphate solution, water, a saturated sodium hydrogen carbonate solution and water, dried over sodium sulphate and concentrated under vacuum. Purification of the residue, carried out by chromatography on a column of silica gel, makes it possible to obtain 0.618 mg of the compound 29.

TLC: $R_f$=0.37, silica gel, 6/1 (v/v) toluene/ethanol.

SCHEME 6 - Synthesis of the oligosaccharide 31

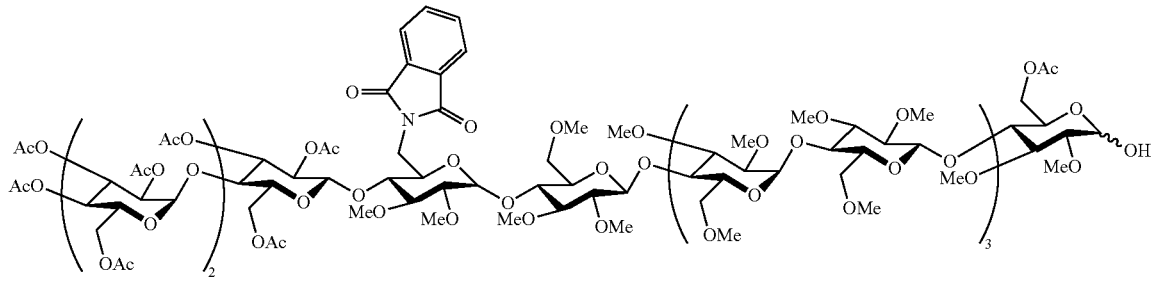

-continued

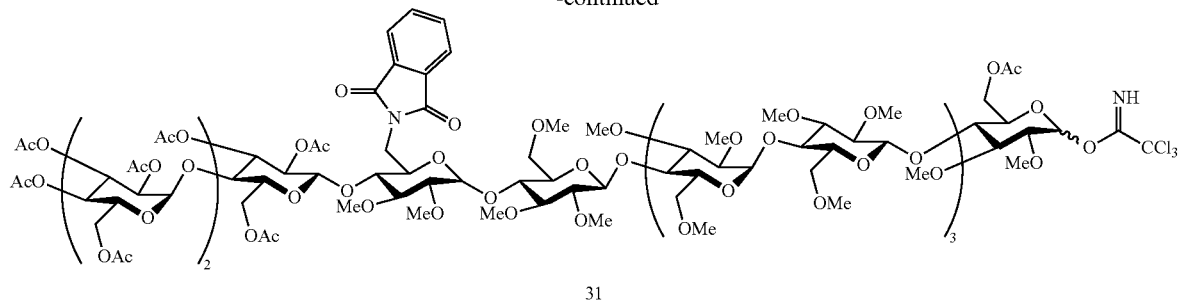

31

PREPARATION 27

(2,3,4,6-Tetra-O-acetyl-α-D-glucopyranosyl)-
(1→4)-(2,3,6-tri-O-acetyl-α-D-glucopyranosyl)-
(1→4)-(2,3,6-tri-O-acetyl-β-D-glucopyranosyl)-
(1→4)-(6-deoxy-2,3-di-O-methyl-6-phthalimido-α-
D-glucopyranosyl)-(1→4)-(2,3,6-tri-O-methyl-β-D-
glucopyranosyl)-(1→4)-[(2,3,6-tri-O-methyl-α-D-
glucopyranosyl)-(1→4)-(2,3,6-tri-O-methyl-β-D-
glucopyranosyl)-(1→4)]$_3$-6-O-acetyl-2,3-di-O-
methyl-D-glucopyranose (30)

A solution of the compound 29 (579 mg, 0.192 mmol) in a 2/1 (v/v) trifluoroacetic acid/dichloromethane mixture (11.5 ml) is stirred for 1 hour. The reaction mixture is diluted with a 2/1 (v/v) toluene/n-propyl acetate mixture (69 ml), concentrated and coevaporated with toluene. The residue is purified by chromatography on a column of silica gel (5/1 (v/v) toluene/ethanol) to produce 523 mg of the compound 30.

TLC: $R_f$=0.31, silica gel, 5/1 (v/v) toluene/ethanol.

PREPARATION 28

(2,3,4,6-Tetra-O-acetyl-α-D-glucopyranosyl)-
(1→4)-(2,3,6-tri-O-acetyl-α-D-glucopyranosyl)-
(1→4)-(2,3,6-tri-O-acetyl-β-D-glucopyranosyl)-
(1→4)-(6-deoxy-2,3-di-O-methyl-6-phthalimido-α-
D-glucopyranosyl)-(1→4)-[(2,3,6-tri-O-methyl-α-D-
glucopyranosyl)-(1→4)-(2,3,6-tri-O-methyl-β-D-
glucopyranosyl)-(1→4)]$_3$-6-O-acetyl-2,3-di-O-
methyl-D-glucopyranose trichloro-acetimidate (31)

Trichloroacetonitrile (65.5 μl, 0.85 mmol) and caesium carbonate (88.4 mg, 0.27 mmol) are added to a solution of the compound 30 in dichloromethane (3 ml). After stirring for 2 hours, the mixture is filtered and concentrated. The residue is purified by chromatography on a column of silica gel (6/1 (v/v) toluene/ethanol+0.1% of triethylamine) to give 477 mg of the compound 31.

TLC: $R_f$=0.35, silica gel, 6/1 (v/v) toluene/ethanol.

SCHEME 7 - Synthesis of the hexadecasaccharide 35
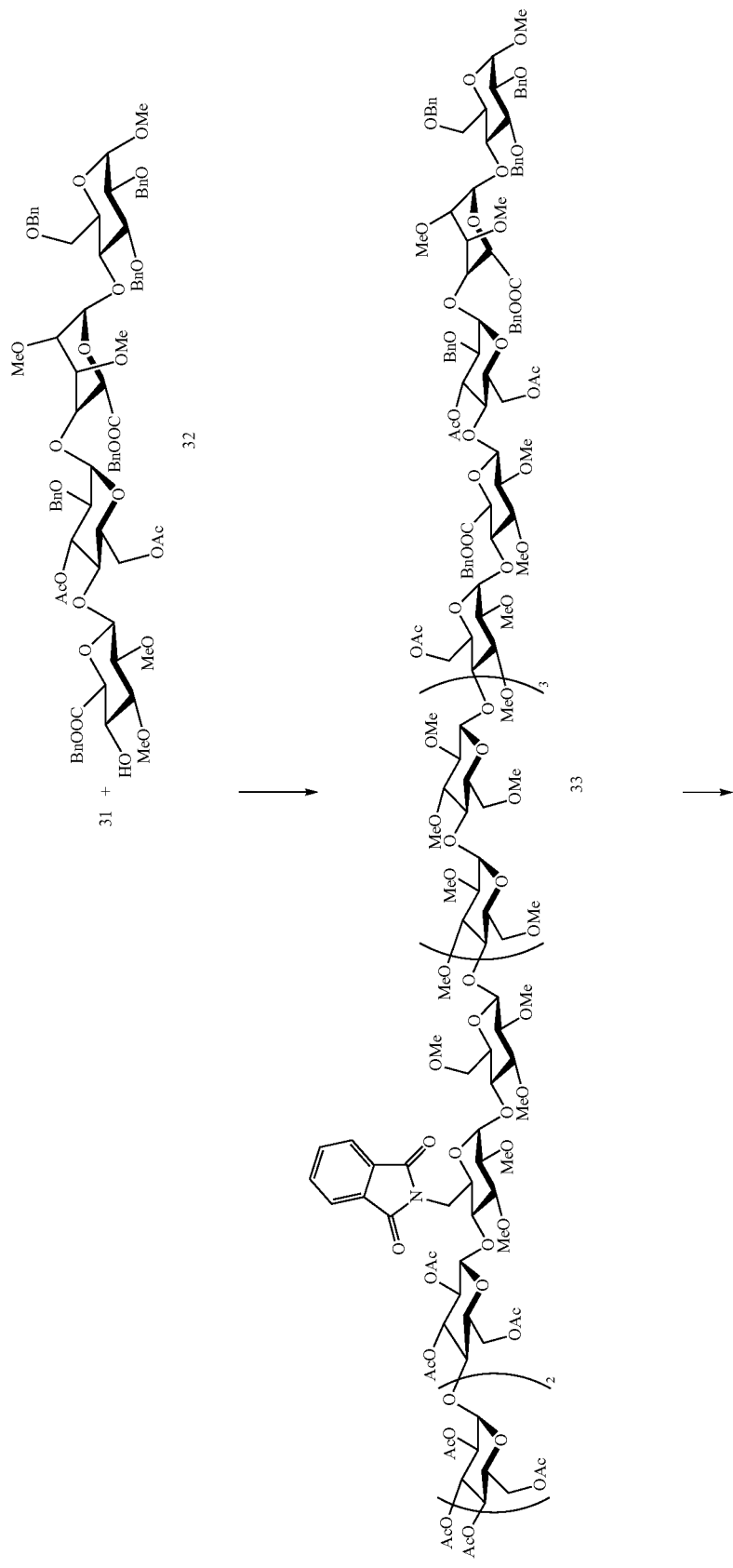

-continued
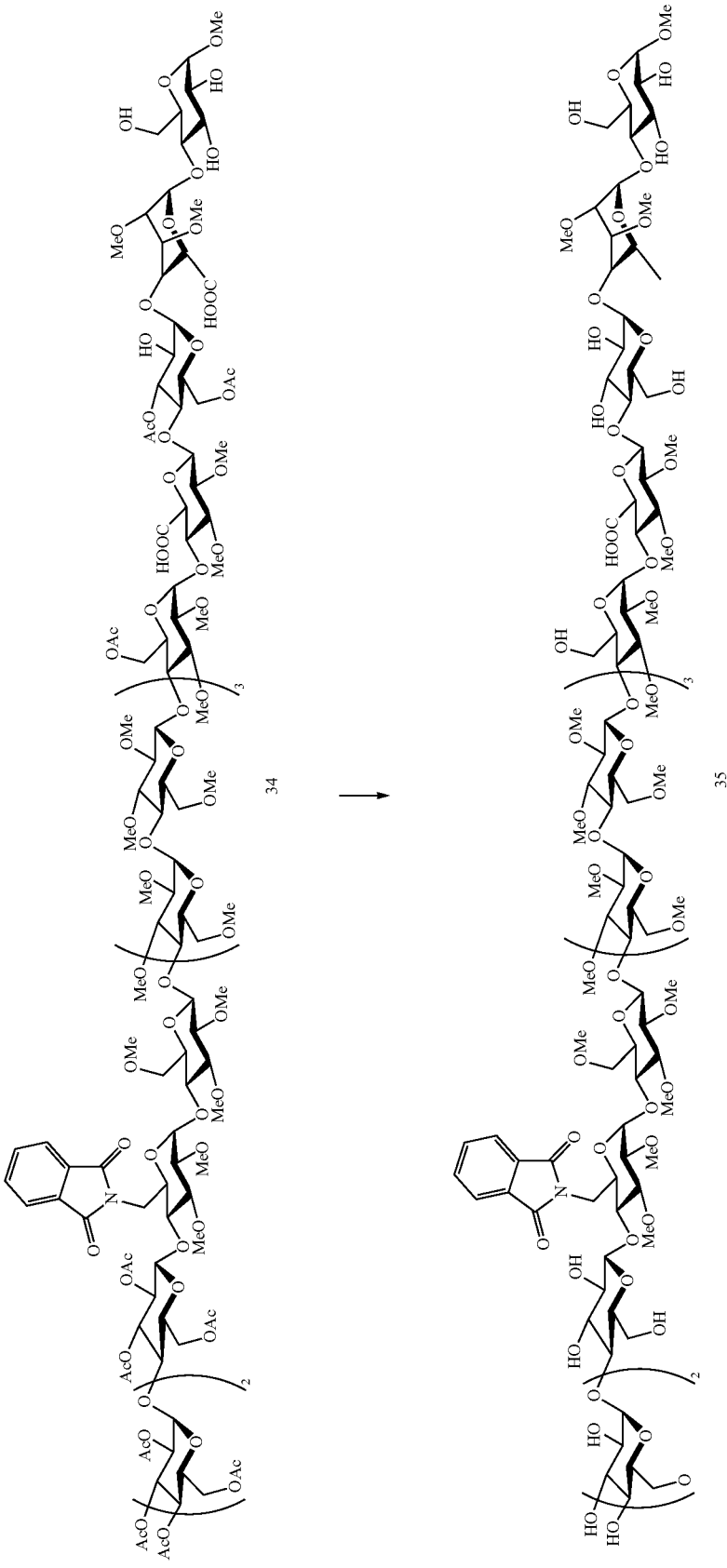

PREPARATION 29

Methyl(2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-deoxy-2,3-di-O-methyl-6-phthalimido-α-D-glucopyranosyl)-(2,3,6-tri-O-methyl-β-D-glucopyranosyl)-(1→4)-[(2,3,6-tri-O-methyl-α-D-glucopyranosyl)-(1→4)-O-(2,3,6-tri-O-methyl-β-D-glucopyranosyl)-(1→4)]$_3$-(6-O-acetyl-2,3-di-O-methyl-α-D-glucopyranosyl)-(1→4)-(benzyl2,3-di-O-methyl-β-D-glucopyranosyluronate)-(1→4)-(3,6-di-O-acetyl-2-O-benzyl-α-D-glucopyranosyl)-(1→4)-(benzyl2,3-di-O-methyl-α-L-idopyranosyluronate)-(1→4)-2,3,6-tri-O-benzyl-α-D-glucopyranoside (33)

The imidate 31 (370 mg, 0.121 mmol) and the compound 32 (336 mg, 0.242 mmol) (obtained according to P. Westerduin et al., BioOrg. Med. Chem., 1994, 2, 1267) are dissolved in a 1/2 (v/v) dichloromethane/diethyl ether mixture (5.5 ml). After addition of 4 Å molecular sieve powder, the mixture is cooled to −20° C. and a 0.1M solution of trimethylsilyl trifluoromethane-sulphonate in dichloromethane (181.5 μl) is added. After 25 minutes, the mixture is neutralized by addition of solid sodium hydrogen carbonate. After filtering and concentrating, the residue is purified by chromatography on Sephadex® LH20 gel, followed by chromatography on a column of silica gel (6/5 (v/v) toluene/acetone) to give 302 mg of the compound 33.

$[\alpha]_D$=+86° (c=1, dichloromethane).

PREPARATION 30

Methyl(2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-deoxy-2,3-di-O-methyl-6-phthalimido-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1-A)-O-(2,3,6-tri-O-methyl-β-D-glucopyranosyl)-(1→4)]$_3$-(6-O-acetyl-2,3-di-O-methyl-α-D-glucopyranosyl)-(1→4)-(2,3-di-O-methyl-β-D-glucopyranosyluronic acid)-1-(3,6-di-O-acetyl-α-D-glucopyranosyl)-(1→4)-(2,3-di-O-methyl-α-L-idopyranosyluronic acid)-(1→4)-α-D-gluco-pyranoside (34)

A solution of the compound 33 (104 mg, 0.024 mmol) in acetic acid (5 ml) is treated under hydrogen pressure (4 bar) in the presence of 10% palladium-on-charcoal (104 mg) for 4 hours. After filtering, the solution is lyophilized to give the compound 34 (87 mg), which is used in the following stage without purification.

PREPARATION 31

Methyl(α-D-glucopyranosyl)-(1→4)-(α-D-glucopyranosyl)-(1→4)-β-D-glucopyranosyl)-(1→4)-(6-deoxy-2,3-di-O-methyl-6-phthalimido-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-O-(2,3,6-tri-O-methyl-β-D-glucopyranosyl)-(1→4)]$_3$-(2,3-di-O-methyl-α-D-glucopyranosyl)-(1→4)-(2,3-di-O-methyl-β-D-glucopyranosyluronic acid)-(1→4)-(α-D-glucopyranosyl)-(1→4)-(2,3-di-O-methyl-α-L-idopyrano-syluronic acid)-(1→4)-α-D-glucopyranoside (35)

A molar solution of sodium methoxide in methanol (140 μl) is added to a solution of the compound 34 (80 mg, 0.021 mmol) in anhydrous methanol (6.9 ml) in the presence of 3 Å molecular sieve powder (875 mg). After 20 hours at ambient temperature, the reaction mixture is filtered and the filtrate is neutralized with acetic acid. The solution is concentrated by half and deposited on a column of Sephadex® G-25 Fine (3×92 cm). After eluting with water and lyophilizing, the compound 35 (66 mg) is obtained.

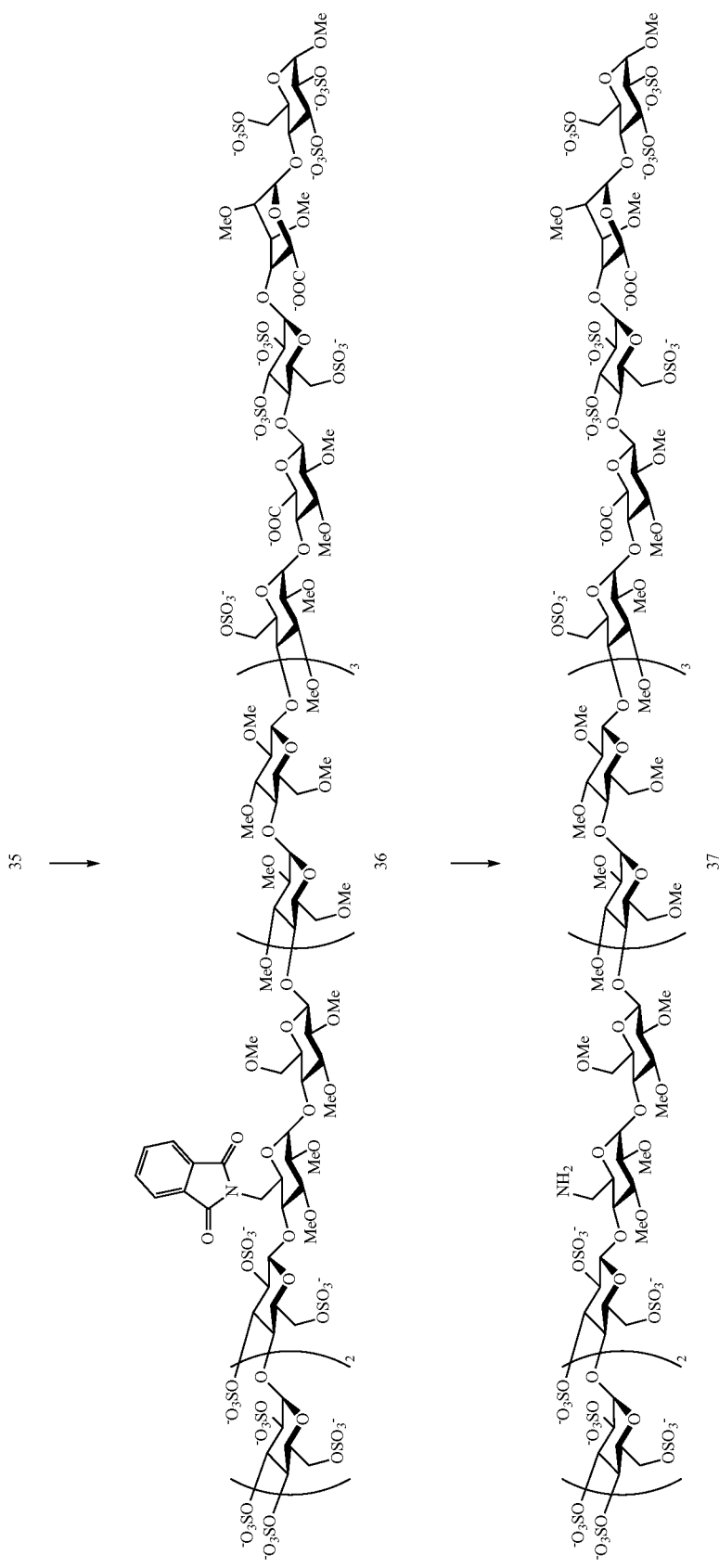

PREPARATION 32

Methyl(2,3,4,6-tetra-O-sulphonato-α-D-glucopyranosyl)-(1→4)-(2,3,6-tri-O-sulphonato-α-D-glucopyranosyl)-(1→4)-(2,3,6-tri-O-sulphonato-β-D-glucopyranosyl)-(1→4)-(6-deoxy-2,3-di-O-methyl-6-phthalimido-α-D-glucopyranosyl)-(1→4)-(2,3,6-tri-O-methyl-β-D-gluco-pyranosyl)-(1→4)-[(2,3,6-tri-O-methyl-α-D-gluco-pyranosyl)-(1→4)-O-(2,3,6-tri-O-methyl-β-D-gluco-pyranosyl)-(1→4)]₃-(6-O-sulphonato-2,3-di-O-methyl-α-D-glucopyranosyl)-(1→4)-(2,3-di-O-methyl-β-D-glucopyrano-syluronic acid)-(1→4)-(2,3,6-tri-O-sulphonato-α-D-glucopyranosyl)-(1→4)-(2,3-di-O-methyl-α-L-idopyrano-syluronic acid)-(1-94)-2,3,6-tri-O-sulphonato-α-D-glucopyranoside, sodium salt (36)

The polyol 35 (66.4 mg, 0.021 mmol) is dissolved in N,N-dimethylformamide (1.8 ml). The sulphur trioxide-triethylamine complex (320 mg, 1.77 mmol) is added and the mixture is stirred for 20 hours at 55° C. The solution is deposited on a column of Sephadex® G-25 Fine (3×92 cm) eluted with 0.2 M sodium chloride. The fractions comprising the product are concentrated and desalting is carried out using the same column eluted with water. After lyophilization, 83 mg of the compound 36 are obtained.

Mass: ESI method, negative mode: chemical mass=4968.92; experimental mass=4966.52±0.16 a.m.u.

PREPARATION 33

Methyl(2,3,4,6-tetra-O-sulphonato-α-D-glucopyranosyl)-(1→4)-(2,3,6-tri-O-sulphonato-α-D-glucopyranosyl)-(1→4)-(2,3,6-tri-O-sulphonato-β-D-glucopyranosyl)-(1→4)-(6-amino-6-deoxy-2,3-di-O-methyl-α-D-glucopyranosyl)-(1→4)-(2,3,6-tri-O-methyl-α-D-gluco-pyranosyl)-(1→4)-[(2,3,6-tri-O-methyl-α-D-gluco-pyranosyl)-(1→4)-O-(2,3,6-tri-O-methyl-β-D-gluco-pyranosyl)-(1→4)]₃-(6-O-sulphonato-2,3-di-O-methyl-α-D-glucopyranosyl)-(1→4)-(2,3-di-O-methyl-β-D-glucopyrano-syluronic acid)-(1→4)-(2,3,6-tri-O-sulphonato-α-D-glucopyranosyl)-(1→4)-(2,3-di-O-methyl-α-L-idopyrano-syluronic acid)-(1→4)-2,3,6-tri-O-sulphonato-α-D-glucopyranoside, sodium salt (37)

The compound 36 (83 mg, 0.017 mmol) is dissolved in a 2/1 (v/v) ethanol/water mixture (1.67 ml). Hydrazine hydrate (81.2 μl, 1.67 mmol) is added and the mixture is brought to reflux for 20 hours. The solution is deposited on a column of Sephadex® G-25 Fine (3×92 cm) eluted with water. After concentrating the fractions comprising the product, the residue is dissolved in 2/1 (v/v) ethanol/water (5.00 ml) and again treated as under the preceding conditions with hydrazine hydrate (81.2 μl) to give 71 mg of the compound 37.

Mass: ESI method, negative mode: chemical mass=4838.32; experimental mass=4814.6±0.70 a.m.u.

SCHEME 9 - Synthesis of the pentasaccharide 39

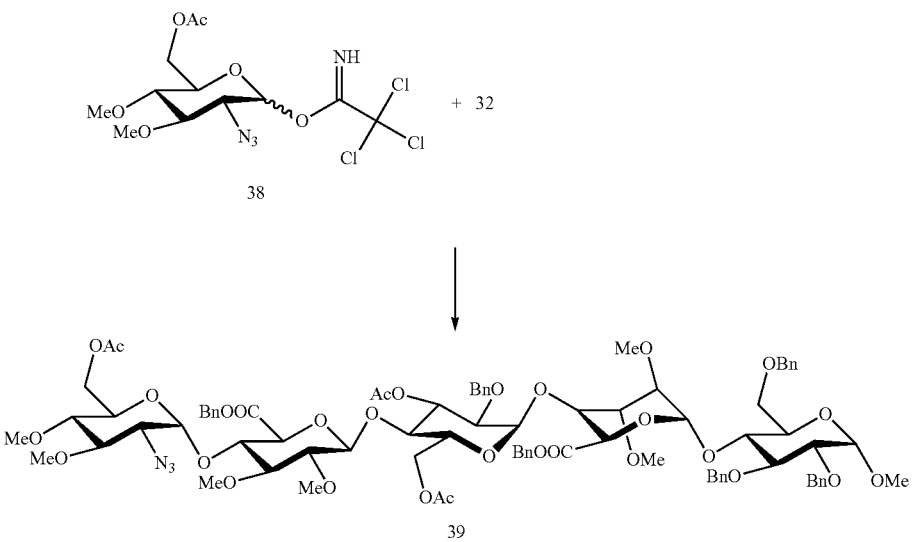

PREPARATION 34

Methyl(6-O-acetyl-2-azido-2-deoxy-3,4-di-O-methyl-α-D-glucopyranosyl)-(1→4)-(benzyl2,3-di-O-methyl-β-D-glucopyranosyluronate)-(1→4)-(3,6-di-O-acetyl-2-O-benzyl-α-D-glucopyranosyl)-(1→4)-(benzyl2,3-di-O-methyl-α-L-idopyranosyluronate)-(1→4)-2,3,6-tri-O-benzyl-α-D-glucopyranoside (39)

The compound 6-O-acetyl-2-azido-2-deoxy-3,4-di-O-methyl-α,β-D-glucopyranose trichloroacetimidate 38 (265 mg, 0.631 mmol) (obtained according to J. Basten et al., *Bioorg. Med. Chem. Lett.* (1992), 2(9), 901) and the compound 32

(584 mg, 0.420 mmol) (obtained according to P. Westerduin et al., *Bioorg. Med. Chem.,* 1994, 2, 1267) are dissolved in a 1/2 (v/v) dichloromethane/diethyl ether mixture (28.5 ml). After addition of 4 Å molecular sieve powder, the mixture is cooled to −20° C. and a 0.1M solution of trimethylsilyl trifluoromethanesulphonate in dichloromethane (94.6 µl) is added. After 10 minutes, imidate (53.8 mg) is again added, followed by a 0.1M solution of trimethylsilyl trifluoromethanesulphonate in dichloromethane (19.2 µl). After 10 minutes, the mixture is neutralized by addition of solid sodium hydrogen carbonate. After filtering and concentrating, the residue is purified by chromatography on a column of silica gel (3/1 (v/v) toluene/ethyl acetate) to give 499 mg of the compound 39.

$[\alpha]_D = +66°$ (c=1.07, dichloromethane).

SCHEME 10 - Synthesis of the pentasaccharide 44

(Process I)

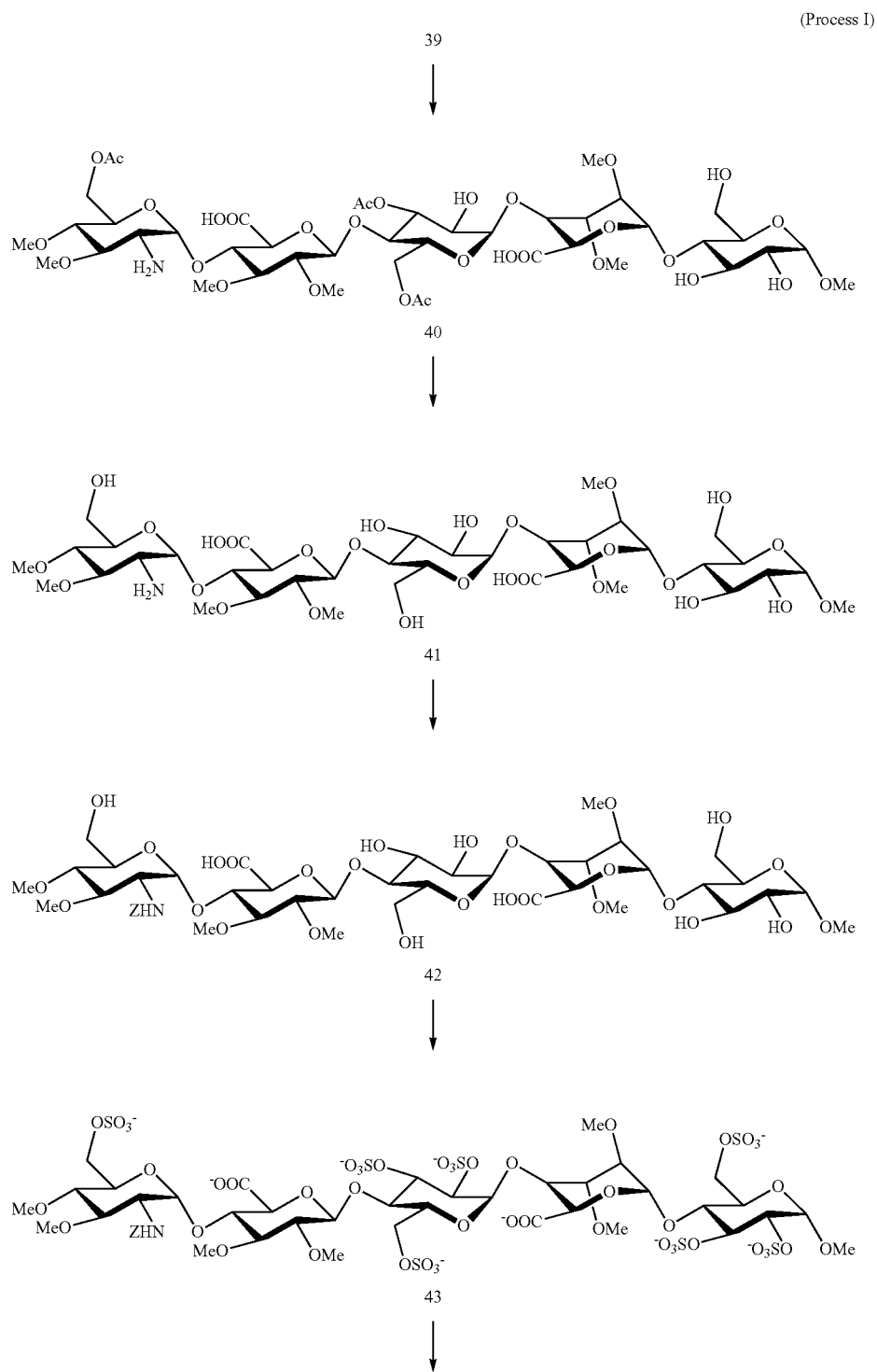

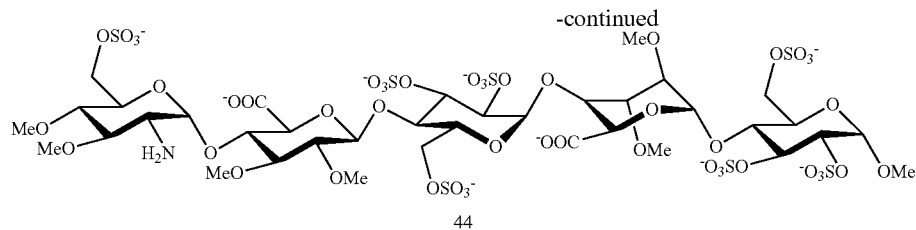

44

PREPARATION 35

Methyl(6-O-acetyl-2-amino-2-deoxy-3,4-di-O-methyl-α-D-glucopyranosyl)-(1→4)-(2,3-di-O-methyl-β-D-glucopyrano-syluronic acid)-(1→4)-(3,6-di-O-acetyl-α-D-gluco-pyranosyl)-(1→4)-(2,3-di-O-methyl-α-L-idopyrano-syluronic acid)-(1→4)-α-D-glucopyranoside (40)

A solution of the compound 39 (552.6 mg, 0.335 mmol) in a 5/1 (v/v) tert-butanol/ethyl acetate mixture (16 ml) is treated under hydrogen pressure (10 bar) in the presence of 10% palladium-on-charcoal (1.10 g) and of 1 M hydrochloric acid (0.336 ml) for 4 hours 30. After filtering, the solution is concentrated and gives the compound 40, which is used in the following stage without purification.

PREPARATION 36

Methyl(2-amino-2-deoxy-3,4-di-O-methyl-α-D-gluco-pyranosyl)-(1→4)-(2,3-di-O-methyl-β-D-glucopyrano-syluronic acid)-(1→4)-(α-D-glucopyranosyl)-(1→4)-(2,3-di-O-methyl-α-L-idopyranosyluronic acid)-(1→4)-α-D-glucopyranoside (41)

The compound 40 (324 mg, 0.300 mmol) is dissolved in methanol (8.8 ml). A 5 M sodium hydroxide solution (2.2 ml) is added and the reaction mixture is stirred at ambient temperature for 16 hours. It is neutralized with a Dowex® 50 H⁺ resin and filtered. The solution is passed through a Sephadex® G-25 Fine column eluted with water. The fractions comprising the product are concentrated and 254.2 mg of the compound 41 are obtained. At this stage, it is confirmed by NMR that the protective groups (benzyl and acetyl groups) have been removed.

TLC: $R_f$=0.26, silica gel, 5/5/1/3 (v/v/v/v) ethyl acetate/pyridine/acetic acid/water.

PREPARATION 37

Methyl(2-(benzyloxycarbonyl)amino-2-deoxy-3,4-di-O-methyl-α-D-glucopyranosyl)-(1→4)-(2,3-di-O-methyl-β-D-glucopyranosyluronic acid)-(1→4)-(α-D-glucopyranosyl)-(1→4)-(2,3-di-O-methyl-α-L-idopyranosyluronic acid)-(1→4)-α-D-glucopyranoside (42)

The compound 41 (241.1 mg, 0.253 mmol) is dissolved in water (12.4 ml) and sodium hydrogen carbonate (63.7 mg) is added, followed dropwise by benzyl chloroformate (41 µl).

After stirring for 12 hours, the reaction mixture is passed through a column of Sephadex® G-25 Fine eluted with water. The fractions comprising the product are concentrated. Purification by chromatography on a column of silica gel (21/17/3.6/10 v/v/v/v ethyl acetate/pyridine/acetic acid/water) gives 221 mg of the compound 42.

TLC: $R_f$=0.63, silica gel, 5/5/1/3 (v/v/v/v) ethyl acetate/pyridine/acetic acid/water.

PREPARATION 38

Methyl(2-(benzyloxycarbonyl)amino-2-deoxy-3,4-di-O-methyl-6-O-sulphonato-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt (43)

The polyol 42 (19.6 mg, 0.018 mmol) is dissolved in N,N-dimethylformamide (1.62 ml). The sulphur trioxide-triethylamine complex (114 mg) is added and the mixture is stirred for 20 hours at 55° C. with light excluded. The solution is deposited on a column of Sephadex® G-25 Fine eluted with 0.2 M sodium chloride. The fractions comprising the product are concentrated and desalting is carried out using the same column eluted with water. After lyophilizing, 28.5 mg of the compound 43 are obtained.

$[\alpha]_D$=+48° (c=2.75, water).

PREPARATION 39

Methyl(2-amino-2-deoxy-3,4-di-O-methyl-6-O-sulphonato-α-D-glucopyranoyl)-(1→4)-(2,3-di-O-methyl-β-D-gluco-pyranosyluronic acid)-(1→4)-(2,3,6-tri-O-sulphonato-α-D-glucopyranosyl)-(1→4)-(2,3-di-O-methyl-α-L-ido-pyranosyluronic acid)-(1→4)-2,3,6-tri-O-sulphonato-α-D-glucopyranoside, sodium salt (44)

A solution of the compound 43 (27.5 mg, 0.015 mmol) in a tert-butanol (333 µl)/water (500 µl) mixture is treated under hydrogen pressure (5 bar) in the presence of 10% palladium-on-charcoal (8.25 mg) for 16 hours. After filtering, the solution is concentrated and the residue is deposited on a column of Sephadex® G-25 Fine (3×92 cm). After eluting with water and lyophilizing, 23.7 mg of the compound 44 are obtained.

$[\alpha]_D$=+58° (c=1, water).

SCHEME 11 - Synthesis of the tetrasaccharide 48

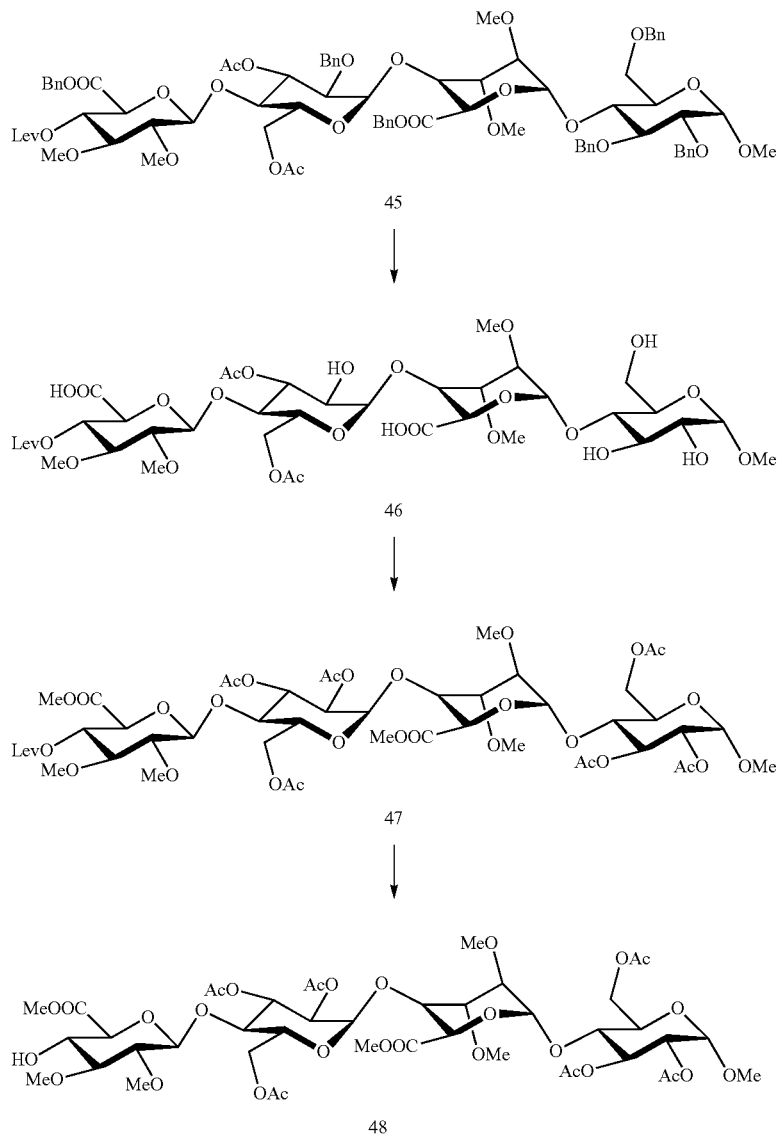

PREPARATION 40

Methyl(4-O-levulinyl-2,3-di-O-methyl-β-D-glucopy-rano-syluronic acid)-(1→4)-(3,6-di-O-acetyl-α-D-gluco-pyranosyl)-(1→4)-(2,3-di-O-methyl-α-L-idopyrano-syluronic acid)-(1→4)-α-D-glucopyranoside (46)

A solution of the compound 45 (4.50 g, 3.02 mmol) (obtained according to P. Westerduin et al., *BioOrg. Med. Chem.*, 1994, 2, 1267) in an ethyl acetate/tert-butanol (72 ml, 1/1, v/v) mixture is treated under hydrogen pressure (4 bar) in the presence of 10% palladium-on-charcoal (9.0 g) for 6 hours. After filtering and concentrating, the compound 46 obtained is used directly in the following stage without purification.

TLC: $R_f$=0.54, 26/22/4.6/17 v/v/v/v ethyl acetate/pyridine/acetic acid/water.

PREPARATION 41

Methyl(methyl4-O-levulinyl-2,3-di-O-methyl-β-D-glucopyranosyluronate)-(1→4)-(2,3,6-tri-O-acetyl-α-D-glucopyranosyl)-(1→4)-(methyl2,3-di-O-methyl-α-L-idopyranosyluronate)-(1→4)-2,3,6-tri-O-acetyl-α-D-glucopyranoside (47)

Potassium hydrogen carbonate (2.71 g) and then methyl iodide (3.4 ml) are added at 0° C. to a solution of the compound 46 (2.57 g, 2.71 mmol) in anhydrous N,N-dimethylformamide (35 ml). After stirring for 16 h at ambient temperature, the reaction mixture is cooled to 0° C. Dimethylaminopyridine (132 mg) and then acetic anhydride (1.5 ml) are subsequently added in succession. The mixture is stirred for 16 h. After neutralizing the excess acetic anhydride, the mixture is diluted with ethyl acetate. The organic phase is washed successively with a 10% potassium hydrogen sulphate solution and water and then with a saturated sodium hydrogen carbonate solution and water, dried over sodium sulphate, filtered and then evaporated to dryness. The residue is purified by chromatography on a column of silica gel [9/5 cyclohexane/(1/1 ethyl acetate/ethanol)] to give 2.51 g of the compound 47.

TLC: $R_f$=0.41, 2/1 v/v toluene/acetone.

PREPARATION 42

Methyl(methyl2,3-di-O-methyl-β-D-glucopyranosyluronate)-(1→4)-(2,3,6-tri-O-acetyl-α-D-glucopyranosyl)-(1→4)-(methyl2,3-di-O-methyl-α-L-idopyranosyluronate)-(1→4)-2,3,6-tri-O-acetyl-α-D-glucopyranoside (48)

The compound 47 (2.5 g, 2.56 mmol) is dissolved in a 1/1 v/v toluene/ethanol mixture (500 ml). Hydrazine acetate (1.01 g) is added. After stirring for 2 h at ambient temperature, the reaction mixture is concentrated to dryness. The residue is dissolved in dichloromethane. The organic phase is washed successively with a 2% sodium hydrogen carbonate solution and water, dried over sodium sulphate, filtered and then evaporated to dryness. After chromatography on a column of silica gel (1/4 v/v toluene/ethyl acetate), 2.01 g of the compound 48 are obtained.

TLC: $R_f$=0.37, 2/1 v/v toluene/acetone.

PREPARATION 43

Methyl(6-O-acetyl-2-azido-2-deoxy-3,4-di-O-methyl-α-D-glucopyranosyl)-(1→4)-(methyl2,3-di-O-methyl-β-D-glucopyranosyluronate)-(1→4)-(2,3,6-tri-O-acetyl-α-D-glucopyranosyl)-(1→4)-(methyl2,3,-di-O-methyl-α-L-idopyranosyluronate)-(1→4)-2,3,6-tri-O-acetyl-α-D-glucopyranoside (49)

The imidate 38 (1.18 g, 2.81 mmol) (obtained according to J. Basten et al., *Bioorg. Med. Chem. Lett.* (1992), 2(9), 901) and the compound 48 (1.83 g, 1.75 mmol) are dissolved in a 1/2 (v/v) dichloromethane/diethyl ether mixture (126 ml). After addition of 4 Å molecular sieve powder, the mixture is cooled to −20° C. and a 1M solution of tert-butyldimethylsilyl trifluoromethanesulphonate in dichloromethane (421 µl) is added. After 30 minutes, a further amount of imidate (266 mg) and a 1M solution of tert-butyldimethylsilyl trifluoromethanesulphonate in dichloromethane (168 µl) are added. After 10 minutes, the mixture is neutralized by addition of solid sodium hydrogen carbonate and filtered. The solution is topped up with dichloromethane, washed successively with a 2% sodium hydrogen carbonate solution and water, dried over sodium sulphate and then concentrated under vacuum. The residue obtained is purified by chromatography on a column of silica gel (4/3 and then 1/1 v/v dichloromethane/ethyl acetate) to give 1.814 g of the compound 49.

TLC: $R_f$=0.57, 3/1 v/v toluene/ethyl acetate.

$[\alpha]_D$=+93° (c=1.15, dichloromethane).

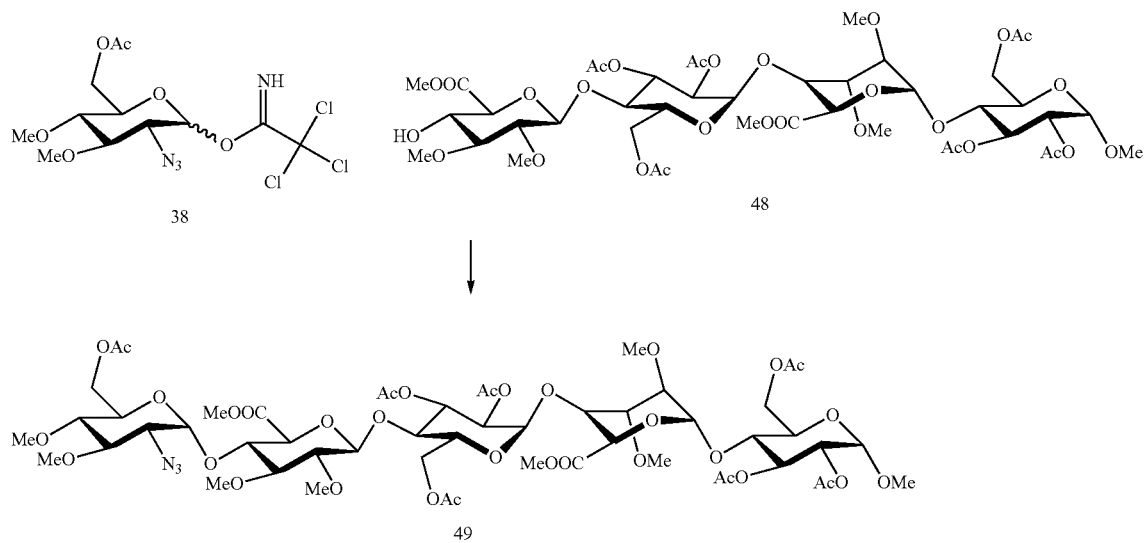

SCHEME 12 Synthesis of the pentasaccharide 49

SCHEME 13 - Synthesis of pentasaccharide 44

(Process II)

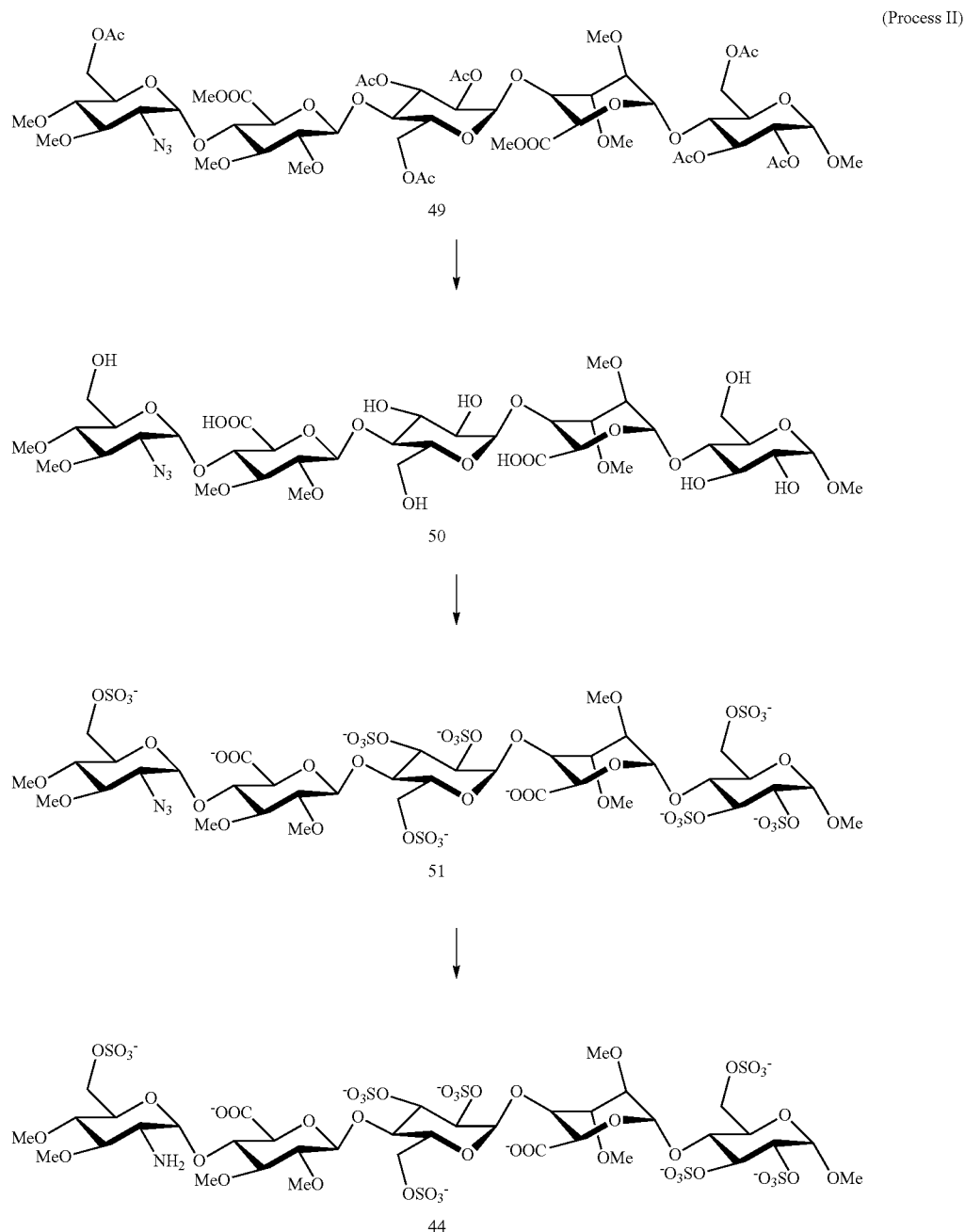

PREPARATION 44

Methyl(2-azido-2-deoxy-3,4-di-O-methyl-α-D-glucopyranosyl)-(1→4)-(2,3-di-O-methyl-β-D-glucopyranosyluronic acid)-(1→4)-(α-D-glucopyranosyl)-(1→4)-(2,3-di-O-methyl-α-L-idopyranosyluronic acid)-(1→4)-α-D-glucopyranoside (50)

30% aqueous hydrogen peroxide solution (42 ml) is added at −5° C. to a solution of the compound 49 (845.3 mg) in tetrahydrofuran (104 ml). After stirring for 5 minutes, a 0.7M aqueous lithium hydroxide solution (19.2 ml) is added dropwise.

The reaction mixture is stirred for 1 h at −5° C., then for 4 h at 0° C. and finally for 16 h at ambient temperature. It is neutralized with a 1 M hydrochloric acid solution.

The solution is deposited on a column of Sephadex® G-25 Fine (5×1 000 cm) eluted with water. The fractions comprising the expected compound are combined, concentrated and deposited on a column of Dowex AG 50 WX4 H$^+$ resin (50 ml). The compound is collected at 0° C. and concentrated to produce 618 mg of the compound 50.

TLC: $R_f$=0.56, 26/22/4.6/17 v/v/v/v ethyl acetate/pyridine/acetic acid/water.

PREPARATION 45

Methyl(2-azido-2-deoxy-3,4-di-O-methyl-6-O-sulphonato-α-D-glucopyranosyl)-(1→4)-(2,3-di-O-methyl-β-D-glucopyranosyluronate)-(1→4)-(2,3,6-tri-O-sulphonato-α-D-glucopyranosyl)-(1→4)-(2,3-di-O-methyl-α-L-idopyranosyluronate)-(1→4)-2,3,6-tri-O-sulphonato-α-D-glucopyranoside, sodium salt (51)

Immediately before using it, the compound 50 is codistilled with N,N-dimethylformamide (3×29 ml). The sulphur trioxide-triethylamine complex (3.84 g) is added to a solution of the compound 50 (612 mg, 0.624 mmol) in N,N-dimethylformamide (58 ml). The mixture is stirred for 16 hours at 55° C. with light excluded. The mixture, cooled to 0° C., is added dropwise to a solution of sodium hydrogen carbonate (5.33 g) in water (200 ml). The mixture is stirred for 16 h at ambient temperature and concentrated to dryness.

The residue is dissolved in water and the solution is deposited on a column of Sephadex® G-25 Fine eluted with 0.2 M sodium chloride. The fractions comprising the product are concentrated and desalting is carried out using the same column eluted with water. After lyophilizing, 1.06 g of the compound 51 are obtained.

TLC: $R_f$=0.5, 3/5/1/3 v/v/v/v ethyl acetate/pyridine/-acetic acid/water.

PREPARATION 46

Methyl(2-amino-2-deoxy-3,4-di-O-methyl-6-O-sulphonato-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3,-di-O-methyl-α-L-idopyranosyluronic acid)-(1→4)-2,3,6-tri-O-sulphonato-α-D-glucopyranoside, sodium salt (44)

This hydrogenolysis was carried out twice and, on each occasion, on 534.4 mg of the compound 51.

A solution of the compound 51 (534.4 mg) in a tert-butanol (6.7 ml, 12.6 ml/g)/water (10 ml, 19 ml/g) mixture is treated under hydrogen pressure (5 bar) in the presence of 10% palladium-on-charcoal (160 mg) at 40° C. for 4 hours. After filtering (Millipore® LSWP 5 □m filter), the solution is concentrated to dryness to give 530 mg of the compound 44.

TLC: $R_f$=0.49, 3/5/1/3 v/v/v/v ethyl acetate/pyridine/-acetic acid/water.

EXAMPLE 1

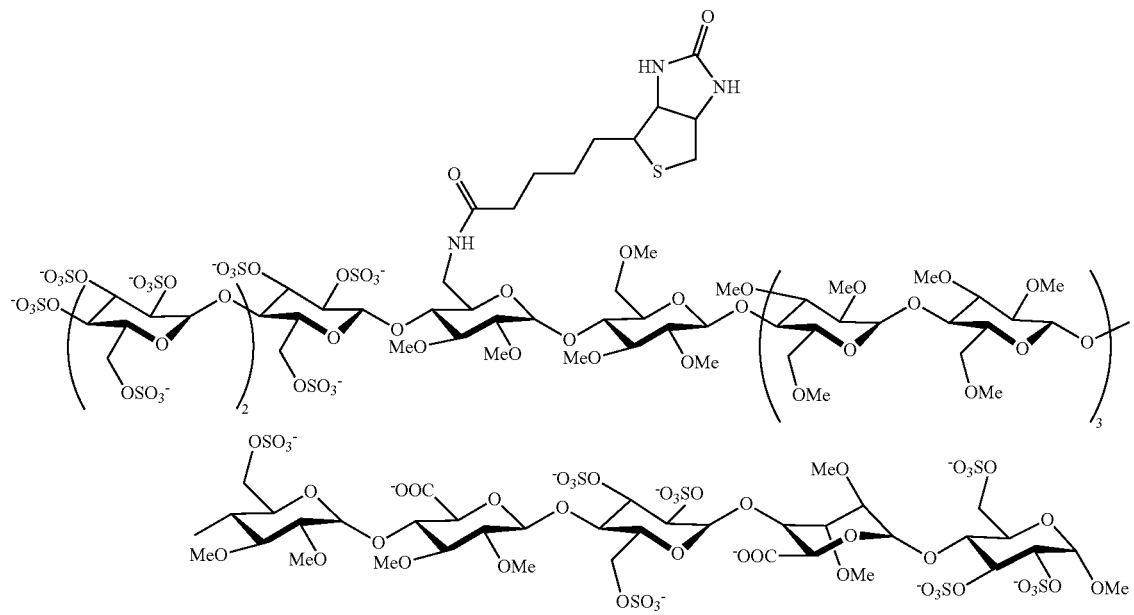

50

EXAMPLE 2

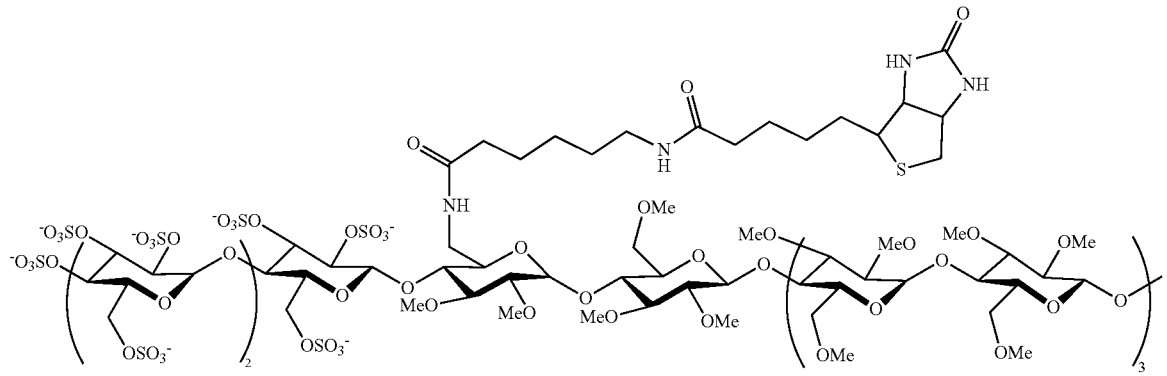

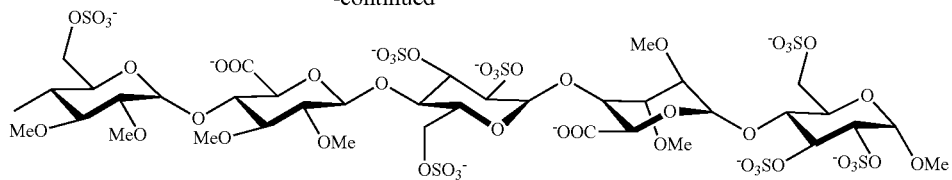
EXAMPLE 3
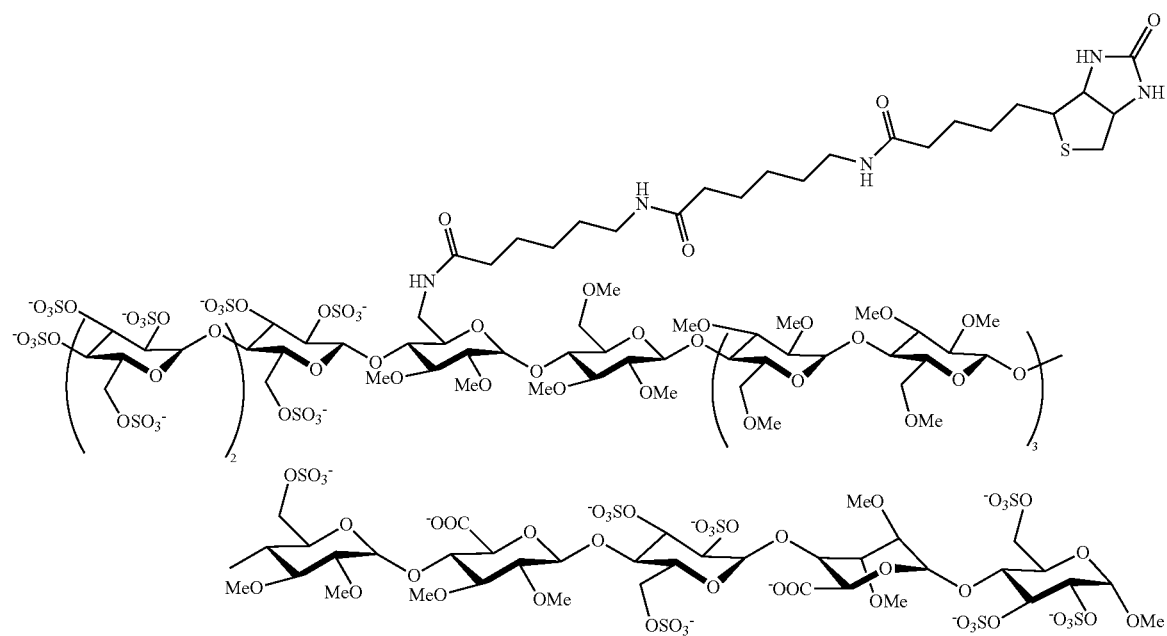
EXAMPLE 4
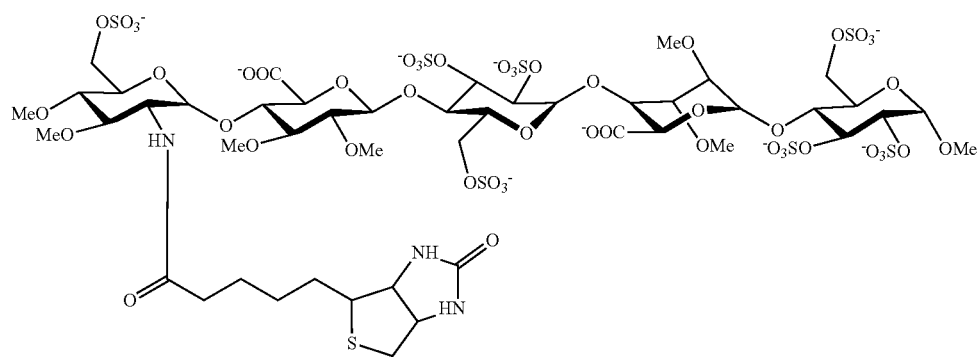

EXAMPLE 5

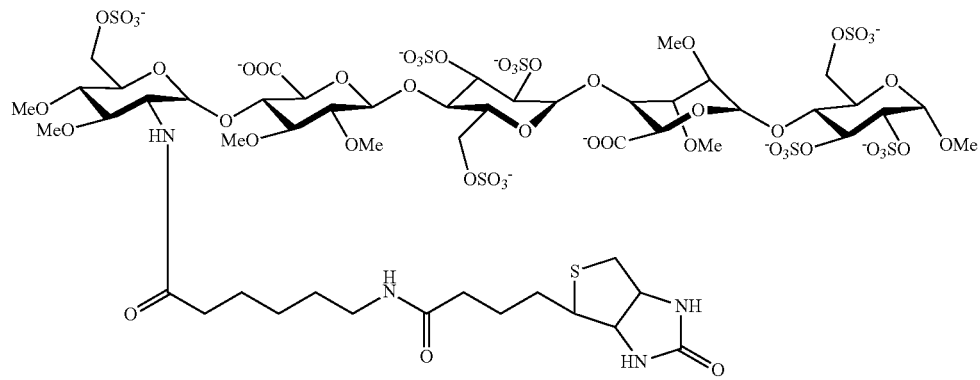

EXAMPLE 6

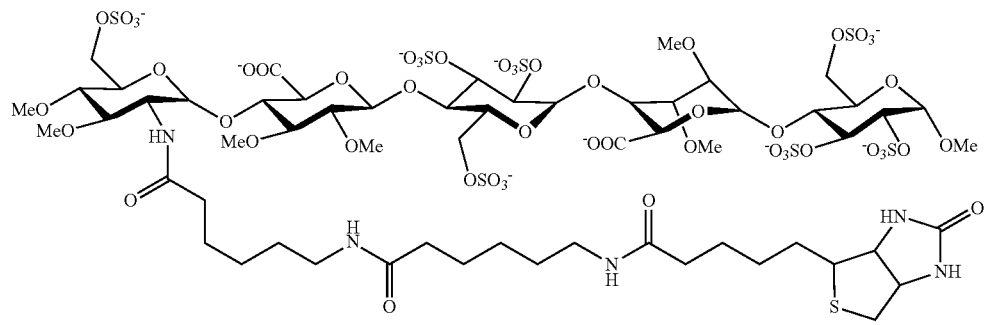

EXAMPLE 1

Methyl(2,3,4,6-tetra-O-sulphonato-α-D-glucopyranosyl)-(1→4)-(2,3,6-tri-O-sulphonato-α-D-glucopyranosyl)-(1→4)-(2,3,6-tri-O-sulphonato-β-D-glucopyranosyl)-(1→4)-(6-biotinamido-6-desoxy-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-O-(2,3,6-tri-O-methyl-β-D-glucopyranosyl)-(1→4)]₃-(6-O-sulphonato-2,3-di-O-methyl-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt Biotin sulphosuccinimide (16.5 mg) is added to a solution of the compound 37 (18 mg, 3.72 nmol) in 0.5% sodium hydrogen carbonate (1.5 ml).

After stirring for 16 hours at ambient temperature, the reaction mixture is deposited on a column of Sephadex® G-25 Fine eluted with sodium chloride.

The fractions comprising the product are concentrated and desalting is carried out on the same column eluted with water.

After lyophilizing, 15.9 mg of the compound of Example 1 are obtained.

[α]$_D$=+59° (c=0.78, water).

Mass: ESI method, negative mode: chemical mass=5065.12; experimental mass=5064.18±1.04 a.m.u.

EXAMPLE 2

Methyl(2,3,4,6-tetra-O-sulphonato-α-D-glucopyranosyl)-(1→4)-(2,3,6-tri-O-sulphonato-α-D-glucopyranosyl)-(1→4)-(2,3,6-tri-O-sulphonato-β-D-glucopyranosyl)-(1→4)-(6-[6-(biotinamido) hexamido]-6-deoxy-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-O-(2,3,6-tri-O-methyl-β-D-glucopyranosyl)-(1→4)₃-(6-O-sulphonato-2,3-di-O-methyl-α-D-glucopyranosyl)-(1→4)-(2,3-di-O-methyl-β-D-glucopyranosylsyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt

[lacuna] 6-(biotinamido)hexanoate (16.5 mg) is added to a solution of the compound 37 (18 mg, 3.72 μmol) in 0.5% sodium hydrogen carbonate (1.5 ml). After stirring for 16 hours at ambient temperature, the reaction mixture is deposited on a column of Sephadex®G-25 Fine eluted with sodium chloride.

The fractions comprising the product are concentrated and desalting is carried out on the same column eluted with water.

After lyophilizing, 17.9 mg of the compound of Example 2 are obtained.

[α]$_D$=+60° (c=1.0, water).
Mass: ESI method, negative mode: chemical mass=5178.28; experimental mass=5176.3±0.77 a.m.u.

EXAMPLE 3

Methyl(2,3,4,6-tetra-O-sulphonato-α-D-glucopyranosyl)-(1→4)-(2,3,6-tri-O-sulphonato-α-D-glucopyranosyl)-(1→4)-(2,3,6-tri-O-sulphonato-β-D-glucopyranosyl)-(1→4)-[6-(6-biotinamidohexamido) hexamido]-6-deoxy-2,3-di-O-methyl-α-D-glucopyranosyl)-(1→4)-(2,3,6-tri-O-methyl-β-D-glucopyranosyl)-(1→4)-[2,3,6-tri-O-methyl-α-D-glucopyranosyl)-(1→4)-O-(2,3,6-tri-O-methyl-β-D-glucopyranosyl)-(1→4)]$_3$-(6-O-sulphonato-2,3-di-O-methyl-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt Sulphosuccinimidyl 6-(6-biotinamidohexamido)hexanoate (23.6 mg) is added to a solution of the compound 37 (17 mg, 3.51 mmol) in 0.5% sodium hydrogen carbonate (1.4 ml).

After stirring for 16 hours at ambient temperature, the reaction mixture is deposited on a column of Sephadex® G-25 Fine eluted with sodium chloride. The fractions comprising the product are concentrated and desalting is carried out on the same column eluted with water.

After lyophilizing, 17.4 mg of the compound of Example 3 are obtained.

[α]$_D$=+64° (c=1.0, water).
Mass: ESI method, negative mode: chemical mass=5291.44; experimental mass=5292.1±0.83 a.m.u.

EXAMPLE 4

Methyl(2-biotinamido-2-deoxy-3,4-di-O-methyl-6-O-sulphonato-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt A solution of biotin N-hydroxysuccinimide (42 mg) in N,N-dimethylformamide (750 μl) is added to a solution of the compound 44 (21.2 mg, 0.012 mmol) in 0.5% sodium hydrogen carbonate (750 μl). After stirring for 16 hours at ambient temperature, the reaction mixture is deposited on a column of Sephadex® G-25 Fine.

After eluting with water and lyophilizing, 22.3 mg of the compound of Example 4 are obtained.

[α]$_D$=+38° (c=0.15, water).
Mass: ESI method, negative mode: chemical mass=1938.48; experimental mass=1937.48±0.11 a.m.u.

EXAMPLE 5

Methyl(2-[N-(6-biotinamidohexanoyl)]-2-deoxy-3,4-di-O-methyl-6-O-sulphonato-α-D-glucopyranoyl)-(1-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium salt This reaction was carried out twice and, on each occasion, on 494.5 mg of the compound 44.

The compound 44 (494.5 mg, 0.289 mmol) is dissolved in a 0.5% aqueous sodium hydrogen carbonate solution (116 ml).

A solution of sulphosuccinimidyl 6-biotinamidohexanoate (1.46 g, 2.63 mmol) in a 0.5% sodium hydrogen carbonate solution (12 ml) is added thereto dropwise. After stirring for 16 hours at ambient temperature, a 1 M aqueous sodium hydroxide solution is added and the mixture is stirred for 1 h. The reaction mixture is deposited on a column of Sephadex® G-25 Fine (5×1 000 cm) eluted with sodium chloride.

The fractions comprising the product and originating from the two reactions are combined.

After lyophilizing, 999.2 mg of the compound of Example 5 are obtained.

TLC: R$_f$=0.42, 3/5/1/3 v/v/v/v ethyl acetate/pyridine/acetic acid/water.

Mass: ESI method, negative mode: chemical mass=2051.64; experimental mass: 2051.60±0.43 a.m.u.

EXAMPLE 6

Methyl(2-[6-(6-biotinamidohexamido)hexamido]-2-deoxy-3,4-di-O-methyl-6-O-sulphonato-α-D-glucopyranosyl)-(1→4)-(2,3-di-O-methyl-β-D-glucopyranosyluronic acid)-(1→4)-(2,3,6-tri-O-sulphonato-α-D-glucopyranosyl)-(1→4)-(2,3-di-O-methyl-α-L-idopyranosyluronic acid)-(1→4)-2,3,6-tri-O-sulphonato-α-D-glucopyranoside, sodium Salt The compound 44 (30.1 mg, 17.6 μmol) is dissolved in a 0.5% aqueous sodium hydrogen carbonate solution (7 ml). A solution of sulphosuccinimidyl 6-(6-biotinamidohexamido)hexanoate (118 mg, 176 μmol) in a 0.5% sodium hydrogen carbonate solution (1 ml) is added thereto dropwise. After stirring for 16 hours at ambient temperature, a 1 M aqueous sodium hydroxide solution is added and the mixture is stirred for 1 h. The reaction mixture is deposited on a Sephadex® G-25 Fine (2×85 cm) column eluted with sodium chloride.

The fractions comprising the product are combined, concentrated and desalted on a Sephadex® G-25 Fine (2×85 cm) column eluted with water.

After lyophilizing, 26.5 mg of the compound of Example 6 are obtained.

Mass: ESI method, negative mode: chemical mass=2164.48; experimental mass: 2164.29±0.38 a.m.u.

The invention claimed is:

1. A method for the treatment of thromboembolic disorders, the method comprising administering to a patient in need thereof a therapeutically effective amount of a synthetic polysaccharide with antithrombotic activity covalently bound to a biotin or a biotin derivative, or a pharmaceutically acceptable salt thereof, wherein the biotin or biotin derivative is comprised of the formula:

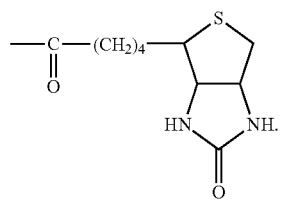

2. The method of claim 1, wherein said thromboembolic disorder is of venous origin.

3. The method of claim 2, wherein said thromboembolic disorder is comprised of a pulmonary embolism.

4. The method of claim 1, wherein said thromboembolic disorder is caused by atherosclerosis and/or diabetes.

5. The method of claim 1, wherein said thromboembolic disorder is caused by one or more conditions selected from the group consisting of angina, apoplexy postangioplasty restenosis, endarterectomy, and the insertion of an endovascular prosthesis.

6. The method of claim 1, wherein the method comprises administering said synthetic polysaccharide as an adjuvant during an endarterectomy that employs a porous balloon.

7. The method of claim 1, wherein said synthetic polysaccharide is a hexadecasaccharide.

8. The method of claim 1, wherein said synthetic polysaccharide is a pentasaccharide.

9. The method of claim 1, wherein said synthetic polysaccharide includes at least one negatively charged group.

10. The method of claim 9, wherein said negatively charged group is selected from sulfate and carboxylate groups.

11. The method of claim 9, wherein said synthetic polysaccharide includes at least one monosaccharide unit that is disulfated or trisulfated.

12. The method of claim 1, wherein said synthetic polysaccharide includes at least one monosaccharide unit that is alkylated.

13. The method of claim 1, further comprising neutralizing the antithrombotic activity of said synthetic polysaccharide, after being administered to said patient, by administering to said patient a dose of avidin or streptavidin effective for neutralizing the antithrombotic activity of said synthetic polysaccharide.

14. The method of claim 1, wherein said synthetic polysaccharide is in the form of a complex with a cyclodextrin.

15. The method of claim 1, wherein the therapeutically effective amount of said synthetic polysaccharide is in a range of 0.1 to 100 mg.

16. The method of claim 1, wherein the therapeutically effective amount of said synthetic polysaccharide is in a range of 0.5 to 50 mg.

* * * * *